US012661378B2

(12) United States Patent
Shen et al.

(10) Patent No.: US 12,661,378 B2
(45) Date of Patent: Jun. 23, 2026

(54) METHODS FOR ENHANCING LIFESPAN AND/OR TREATING CELLULAR PROLIFERATIVE DISORDERS BY TRANSPLANTATION

(71) Applicant: ACADEMIA SINICA, Taipei (TW)

(72) Inventors: Che-Kun James Shen, Taipei City (TW); Yu-Chiau Shyu, Keelung (TW); Chun-Hao Hung, Tainan City (TW)

(73) Assignee: ACADEMIA SINICA, Taipei (TW)

( * ) Notice: Subject to any disclaimer, the term of this patent is extended or adjusted under 35 U.S.C. 154(b) by 1106 days.

(21) Appl. No.: 17/587,685

(22) Filed: Jan. 28, 2022

(65) Prior Publication Data

US 2022/0143102 A1    May 12, 2022

Related U.S. Application Data

(63) Continuation of application No. 16/333,186, filed as application No. PCT/US2017/051310 on Sep. 13, 2017, now Pat. No. 11,266,697.

(60) Provisional application No. 62/393,665, filed on Sep. 13, 2016.

(51) Int. Cl.
| | |
|---|---|
| *A61K 35/545* | (2015.01) |
| *A61P 35/00* | (2006.01) |
| *C07K 14/47* | (2006.01) |
| *C12N 5/0735* | (2010.01) |
| *C12N 5/074* | (2010.01) |
| *C12N 5/0775* | (2010.01) |
| *C12N 5/0789* | (2010.01) |

(52) U.S. Cl.
CPC ............ *A61K 35/545* (2013.01); *A61P 35/00* (2018.01); *C07K 14/47* (2013.01); *C07K 14/4702* (2013.01); *C12N 5/0606* (2013.01); *C12N 5/0647* (2013.01); *C12N 5/0663* (2013.01); *C12N 5/0665* (2013.01); *C12N 5/0696* (2013.01); *C12N 2501/125* (2013.01); *C12N 2501/2303* (2013.01); *C12N 2501/2306* (2013.01); *C12N 2501/60* (2013.01); *C12N 2510/00* (2013.01)

(58) Field of Classification Search
None
See application file for complete search history.

(56) References Cited

U.S. PATENT DOCUMENTS

| | | | | |
|---|---|---|---|---|
| 11,266,697 | B2 * | 3/2022 | Shen ..................... | C12N 5/0696 |
| 2014/0018410 | A1 | 1/2014 | Novobrantseva et al. | |

FOREIGN PATENT DOCUMENTS

| | | | |
|---|---|---|---|
| WO | 2001/034843 | A1 | 5/2001 |
| WO | 2004/071464 | A2 | 8/2004 |
| WO | 2016/036727 | A1 | 3/2016 |
| WO | 2017079591 | A2 | 5/2017 |

OTHER PUBLICATIONS

International Search Report and Written Opinion in International Patent Application No. PCT/US17/51310, dated Nov. 27, 2017, in 29 pages.
Frontelo, Pilar, et al. "Novel role for EKLF in megakaryocyte lineage commitment." Blood 110.12 (2007): 3871-3880.
Yao, Huilan, et al. "Corepressor Rcor1 is essential for murine erythropoiesis." Blood 123.20 (2014): 3175-3184.
Wang, Tao-Yeuan, et al. "Unique biological properties and application potentials of CD34+ CD38—stem cells from various sources." Taiwanese Journal of Obstetrics and Gynecology 48.4 (2009): 356-369.
Porcu, Susanna, et al. "Klf1 affects DNase II-alpha expression in the central macrophage of a fetal liver erythroblastic sland: a non-cell-autonomous role in definitive erythropoiesis." Molecular and Cellular Biology 31.19 (2011): 4144-4154.
Thomson, James A., et al. "Embryonic stem cell lines derived from human blastocysts." Science 282.5391 (1998): 1145-1147.
Thomson, James A., and Vivienne S. Marshall. "4 Primate Embryonic Stem Cells." Current Topics in Developmental Biology. vol. 38. Academic Press, 1998. 133-165.
Reubinoff, Benjamin E., et al. "Embryonic stem cell lines from human blastocysts: somatic differentiation in vitro." Nature Biotechnology 18.4 (2000): 399-404.
Anam, Khairul, and Thomas A. Davis. "Comparative analysis of gene transcripts for cell signaling receptors in bone marrow-derived hematopoietic stem/progenitor cell and mesenchymal stromal cell populations." Stem Cell Research & Therapy 4.5 (2013): 112, 13 pages.
Ghiaur, Gabriel, et al. "Regulation of human hematopoietic stem cell self-renewal by the microenvironment's control of retinoic acid signaling." Proceedings of the National Academy of Sciences 110.40 (2013): 16121-16126.
Kent, David G., et al. "Self-renewal of single mouse hematopoietic stem cells is reduced by JAK2V617F without compromising progenitor cell expansion." PLoS biology 11.6 (2013): e1001576, 15 pages.
Liou, Yae-Huei, et al. "Adipocyte IL-15 regulates local and systemic NK cell development." The Journal of Immunology 193.4 (2014): 1747-1758.
Miller, Cindy L., and Becky Lai. "Human and mouse hematopoietic colony-forming cell assays." Methods in Molecular Biology, vol. 290 Basic Cell Culture Protocols, Third Edition, Humana Press, 2005. 71-89.

(Continued)

*Primary Examiner* — Blaine Lankford
(74) *Attorney, Agent, or Firm* — DUANE MORRIS LLP

(57) ABSTRACT

The invention found that first, the feasibility of transfer of tumor resistance and other healthy longevity characters through transplantation of bone marrow mononuclear cells (BMMNC) or hematopoietic stem cells (HSC)/hematopoietic stem and progenitor cells (HSPC) consisting of genetically engineered EKLF gene encoding the hematopoietic transcription factor EKLF. Secondly, the present invention demonstrates expression of EKLF in the long-term hematopoietic stem cells (LT-HSC), and thus EKLF as a target of regulation of hematopoiesis.

12 Claims, 9 Drawing Sheets

Specification includes a Sequence Listing.

(56)               References Cited

OTHER PUBLICATIONS

Shyu, Yu-Chiau, et al. "Tight regulation of a timed nuclear import wave of EKLF by PKC$\theta$ and FOE during Pro-E to Baso-E transition." Developmental Cell 28.4 (2014): 409-422.

Wang, Tao, et al. "The control of hematopoietic stem cell maintenance, self-renewal, and differentiation by Mysm1-mediated epigenetic regulation." Blood 122.16 (2013): 2812-2822.

Extended European Search Report in EP counterpart Application No. 17851436.0, dated Apr. 6, 2020, in 8 pages.

Siatecka, Miroslawa, Li Xue, and James J. Bieker. "Sumoylation of EKLF promotes transcriptional repression and is involved in inhibition of megakaryopoiesis." Molecular and Cellular Biology 27.24 (2007): 8547-8560.

Office Action in Japan counterpart application No. 2019-535208, dated May 8, 2020, in 3 pages; machine translation provided.

* cited by examiner (B)

(C)

(A)

(B)

METHODS FOR ENHANCING LIFESPAN AND/OR TREATING CELLULAR PROLIFERATIVE DISORDERS BY TRANSPLANTATION

CROSS-REFERENCE TO RELATED APPLICATION

This application is a Continuation of U.S. application Ser. No. 16/333,186, filed Mar. 13, 2019, which was a 371 National Stage Entry of International Application PCT/US2017/051310, filed Sep. 13, 2017, which claimed the benefit of U.S. Provisional Application 62/393,665, filed Sep. 13, 2016, which are all incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is LELIWOTEMP_SQL_ST25.txt. The text file is 4 KB, was created on Sep. 13, 2017, and is being submitted electronically via EFS-Web.

FIELD OF THE INVENTION

The invention is related to the field of stem cells. Particularly, the invention pertains to transfer of tumor resistance and healthy longevity to a subject through transplantation (such as bone marrow transplantation or pluripotent stem cell transplantation) of hematopoietic stem cells (HSCs) and/or hematopoietic stem and progenitor cells (HSPCs) carrying a modified Eklf gene encoding the EKLF polypeptide.

BACKGROUND OF THE INVENTION

Hematopoiesis is the process in which the hematopoietic/blood system generates multiple types of myeloid and lymphoid blood cells. The lymphoid and myeloid lineage commitment occurs in multipotent hematopoietic progenitors including the multipotent progenitor (MPP), the common myeloid progenitor (CMP), the myeloid/erythroid progenitor (MEP), the granulocyte/macrophage progenitor (GMP), and the common lymphoid progenitor (CLP), with MPP generated through self-renewal and differentiation of the hematopoietic stem cells (HSC). HSC primarily resides in the GO phase under homeostatic conditions. Being at the very top of the hematopoietic cellular system, HSC plays a major role in hematopoiesis, and the regulation of its homeostasis determines the downstream fates of various hematopoietic/blood cells. Notably, a number of cytokines (such as IL-3, IL-7, SCF, TPO and GM-CSF, etc.) and transcription factors (such as Notch1, Tal-1, HoxB4, GATA1, GATA2, and GATA3, etc.) are involved in the regulation of homeostasis of HSC and hematopoietic progenitors. The morphologic and functional properties of purified HSC have been extensively characterized. Also, a number of studies have been reported on the regulation of the self-renewal, maintenance, and differentiation of HSC on the molecular and cellular levels.

Longevity genes are of obvious interest and importance, both for their life-extension potential and the possibility of enhancing quality of life. However, very few of these genes have been identified and even less is understood about how these genes act to prevent aging and promote life extension. WO 2016036727 provides a non-human transgenic animal comprising one or more modified Erythroid Kruppel-like factor (EKLF) genes encoding a modified EKLF polypeptide comprising one or more amino acid modifications as compared to a wild-type EKLF polypeptide. The genetically altered EKLF mice display extended lifespan, extended healthspan, and resistance to cancer incidence and/or metastasis. Thus, the modified Eklf genes and their products are useful for preventing aging and treating tumors.

EKLF/KLF1 is the first member of the Krüppel-like factor family consisting of N-terminal activation domain, C-terminal zinc finger domain, and multiple post-translational modification sites. Genome-wide analysis of mouse fetal liver has identified a number of genes the activation or repression of which are regulated through DNA-binding of EKLF to specific regulatory regions. EKLF/KLF1 was identified initially as an erythroid-specific transcription factor, but later found to also be expressed in megakaryocyte and hematopoietic progenitors including MEP, GMP, as well as CMP (Frontelo, P., Manwani, D., Galdass, M., Karsunky, H., Lohmann, F., Gallagher, P. G., and Bieker, J. J. (2007). *Novel role for EKLF in megakaryocyte lineage commitment. Blood* 110, 3871-3880). Loss-of-function and gain-of-function studies have shown that EKLF not only regulates the process of erythropoiesis (Porcu, S., Manchinu, M. F., Marongiu, M. F., Sogos, V., Poddie, D., Asunis, L, Porcu, L., Marini, M. G., Moi, P., Cao, A., et al. (2011). *Klf1 affects DNase H1-alpha expression in the central macrophage of a fetal liver erythroblastic island: a non-cell-autonomous role in definitive erythropoiesis. Mol Cell Biol* 31, 4144-4154), but also the differentiation fate decision from MEP to erythrocyte or megakaryocyte.

However, whether and how extensively EKLF participates in the regulation of hematopoiesis other than the megakaryocyte-erythrocyte separation and monocyte-to-macrophage remains unknown.

SUMMARY OF THE INVENTION

The present invention pertains to, first, the feasibility of transfer of tumor resistance and other healthy longevity characters through transplantation of bone marrow mononuclear cells (BMMNC) or hematopoietic stem cells (HSC)/hematopoietic stem and progenitor cells (HSPC) consisting of genetically engineered Eklf gene encoding the hematopoietic transcription factor EKLF. Secondly, it pertains to the demonstration of expression of EKLF in the long-term hematopoietic stem cells (LT-HSC), and thus EKLF as a target of regulation of hematopoiesis.

The homeostasis of the hematopoietic system depends in part on the balance of the self-renewal of LT-HSC and proliferation of the different hematopoietic precursors with their differentiation capabilities, which are modulated by various cytokines and signal transduction pathways. The invention found that EKLF is expressed at a relatively high level in long-term hematopoietic stem cells (LT-HSC), which are at the very top of the differentiation program of the hematopoietic/blood system. The invention also found that depletion of EKLF leads to population changes of different types of the hematopoietic/blood cells, in particular decrease of LT-HSC and increase of hematopoietic progenitors. Therefore, tumor resistance and healthy longevity could be transferred through bone marrow transplantation or stem transplantation of HSC/HSPC carrying the genetically engineered Eklf gene encoding the hematopoietic transcription factor EKLF.

Accordingly, the present invention provides a method of increasing longevity and/or inhibiting or reducing tumor occurrence or tumor metastasis of a subject, comprising: (a) genetically engineering embryonic stem cells (ESCs), induced pluripotent cells (iPSCs) and/or cord blood stem cells (CBSCs) to possess one or more modified Erythroid Kruppel-like factor (Eklf) genes encoding a modified EKLF polypeptide comprising one or more amino acid modifications as compared to a wild-type EKLF polypeptide; (b) differentiating the genetically engineered ESCs, iPSCs, and/ or CSBCs to obtain hematopoietic stem cells (HSCs) and/or hematopoietic stem and progenitor cells (HSPCs); and (c) transplanting the HSCs and/or HSPCs to a subject; whereby the transplanted HSCs and/or HSPCs confer healthy longevity and/or tumor resistance or metastasis resistance to the subject.

The present also provides a method of increasing longevity and/or inhibiting or reducing tumor occurrence or tumor metastasis of a subject, comprising: (a) collecting bone marrow from a donor subject comprising one or more modified Eklf genes encoding a modified EKLF polypeptide comprising one or more amino acid modifications as compared to a wild-type EKLF polypeptide; (b) isolating bone marrow mononuclear cells (BMMNCs) comprising HSCs and/or HSPCs HSC and/or HSPC carrying the one or more modified Eklf genes; and (c) transplanting the BMMNCs to a receipt subject, whereby the receipt subject is conferred with tumor resistance and/or healthy longevity.

Accordingly, the invention provides a cell engineered with a gene encoding a EKLF polypeptide, which comprises at least one amino acid modification as compared to a wild type EKLF polypeptide, wherein the cell is an ESC, an iPSC, a CBSC, a HSC, a HSPC or a BMMNC.

In some embodiments, the one or more amino acid modification comprises a modification of an amino acid corresponding to position 74 of the full length wild-type mouse EKLF polypeptide. In certain embodiments related to animals other than mice, the one or more amino acid modification comprises a modification of a sumoylated amino acid residue corresponding to this residue in the mouse EKLF polypeptide, but it may be located at a different position. For example, in the human EKLF polypeptide, the sumoylation site corresponding to position 74 in the mouse EKLF polypeptide is located at amino acid residue 54. In particular embodiments, it is a Lys residue. In certain embodiments, the modification of the amino acid corresponding to position 54 or 74 is a substitution of Lys with Arg (K54R or K74R) or with another amino acid that confers tumor resistance and healthy longevity.

In some embodiments, the cells are transduced to express the modified EKLF polypeptide via use of a viral vector encoding the modified EKLF polypeptide or via use of clustered regularly interspaced short palindromic repeats (CRISPR) and CRISPR associated proteins (Cas) system.

In one embodiment, the expression of the modified EKLF polypeptide leads to enhanced lifespan, anti-metastasis, and/ or anti-tumorigenesis.

In one embodiment, the EKLF is expressed at a relatively high level in LT-HSCs and depletion of EKLF leads to population changes of different types of hematopoietic/ blood cells. In another embodiment, the EKLF negatively regulates the expression of colony-stimulating factor 2 receptor subunit Csf2rb in LT-HSC and the hematopoietic progenitors (such as MPP, CMP, GMP, and MEP).

DETAILED DESCRIPTION OF THE INVENTION

Figure 1:
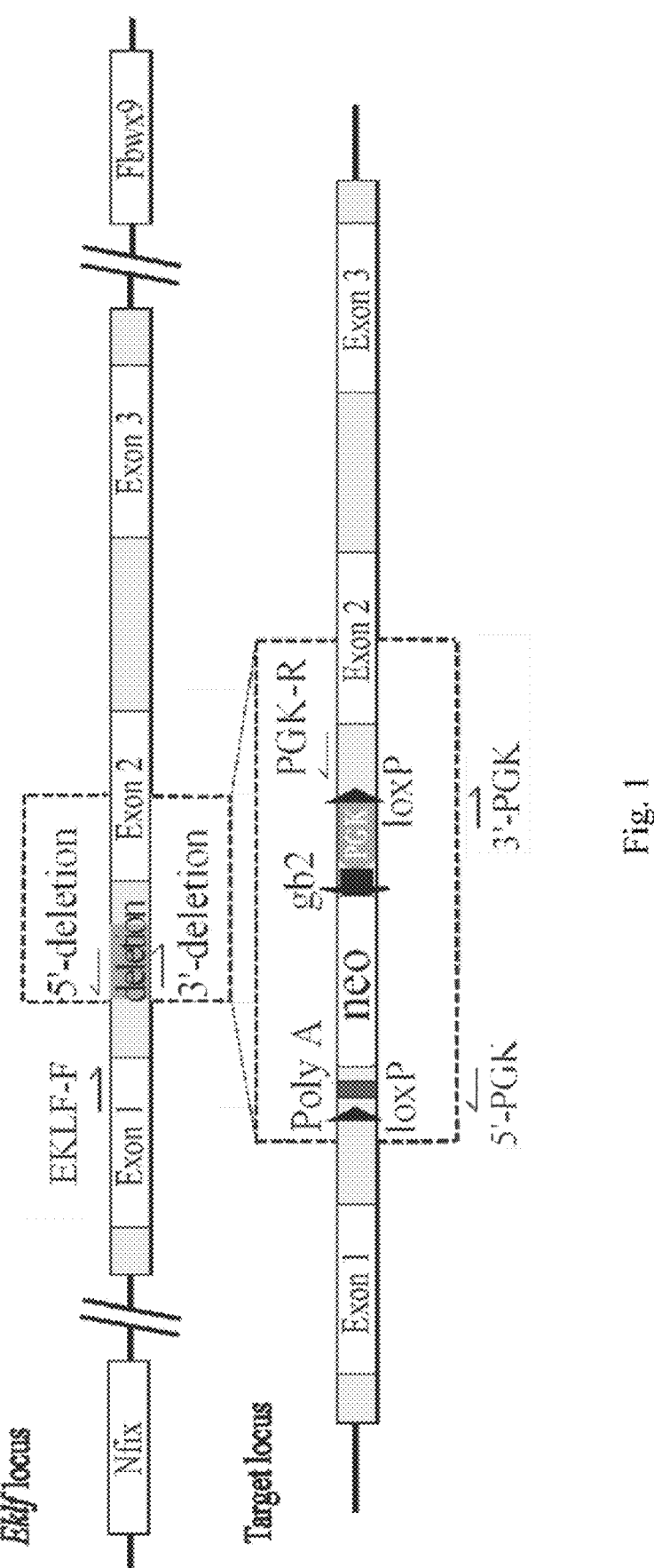
FIGS. 1 (A) to (C) show generation of mice with gene knockout (KO) of Eklf. (A) Targeting strategy. The schematic diagram shows the genetic context of Eklf locus and the map of the targeting BAC construct harboring an inverted loxP-PGK-gb2-neo-loxP cassette in the intron 1 region of Eklf gene. For PCR-based genotyping, 50 bp deletion (gray block) was introduced into intron 1 after the 5' end of LoxP site. The locations of the PCR primers used for genotyping are shown as small black arrows: 5'-deletion: 5'-GCG GCG CGA TAA CTT CGT AT-3' (SEQ ID NO: 1), 5'-PGK: 5'-TTG AAT TCT GCT TCC TGT TGG A-3' (SEQ ID NO: 2), EKLF-F: 5'-AGG CAG AAG AGA GAG AGG AGG C-3' (SEQ ID NO: 3), 3'-deletion: 5'-CCT ATT TCT CCA ACA GGA AGC A-3' (SEQ ID NO: 4), PGK-R: 5'-CTG GCC CTC AAA CAA CCC TG-3' (SEQ ID NO: 5), 3'-PGK: 5'-GTT ATG CGG CCC TAG TGA TTT A-3' (SEQ ID NO: 6). Nifx and Fbwx9 are two distal gene loci flanking the Eklf locus. neo, neomycin resistance gene; PGK, phosphoglycerate kinase I promoter; black arrow, the prokaryotic promoter gb2; black arrow heads, loxP sites. (B) Left panels, anemic phenotype of the homozygous Eklf$^{-/-}$ (KO). E14.5 embryo in comparison to the WT E14.5 embryo. Right upper 2 panels, genotyping of E14.5 embryos. Tail genomic DNAs were amplified by PCR using specific primers for the wild-type (5'-PGK and 3'-PGK) and mutant (5'-deletion and 3'-deletion). +/+, wild-type; +/−, heterozygous Eklf$^{+/-}$; −/−, homozygous Eklf$^{-/-}$. Right lower 2 panels, immunoblotting (IB) analysis showing the depletion of EKLF protein expression by Eklf gene knockout. β-actin was used as an internal control. (C) Comparative FACS analysis of E14.5 fetal liver cells of the WT and Eklf$^{-/-}$ mice. Note the decrease of Ter119$^+$ cells of the erythroid lineage and increase of CD41$^+$, CD42d$^+$ magakarocytes in the Eklf$^{-/-}$ E14.5 fetal liver, which is similar to the report by Frontelo et al. (2007). N=3.
Figure 1:
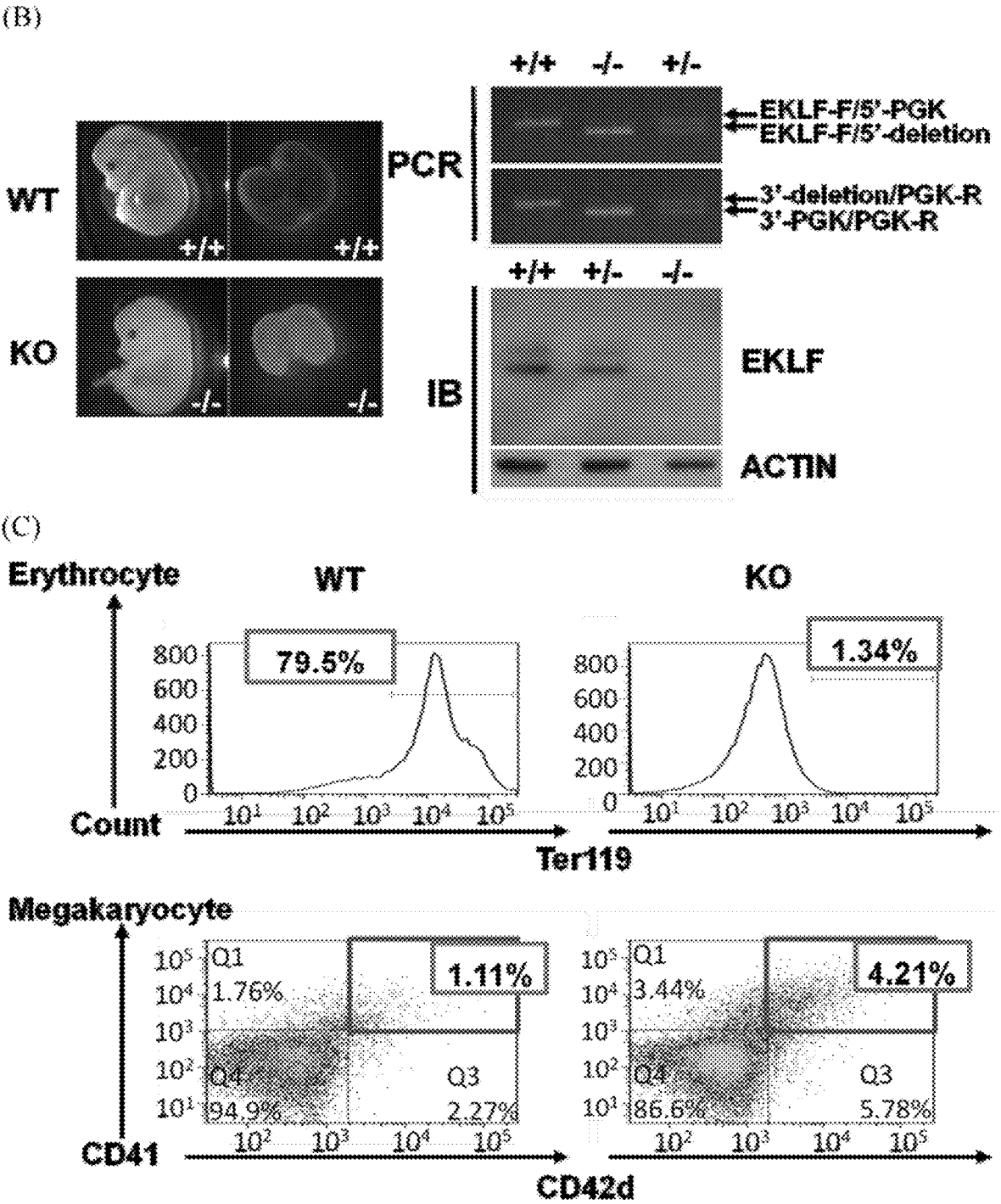

For convenience, certain terms employed in the context of the present disclosure are collected here. Unless defined otherwise, all technical and scientific terms used herein have the same meaning as commonly understood by one of the ordinary skill in the art to which this invention belongs.

The singular forms "a", "and", and "the" are used herein to include plural referents unless the context clearly dictates otherwise.

Definitions

As used herein, the term "expression" is intended to refer to transcription of a gene when a condition is met, resulting in the generation of mRNA and usually encoded protein. Expression can be achieved or performed naturally by the cell (i.e., without artificially intervention) or may be achieved or performed artificially (i.e., with the involvement of artificially intervention, such as by the use of promoters regulated by the use of a chemical agent). The expression may also be initiated by a recombination event triggered by a site-specific recombinase, such as by Cre-mediated recombination. Expression may be measured by measuring mRNA transcribed from the gene or by measuring protein encoded by the gene.

As used herein, the term "nucleic acid" refers to polynucleotides such as deoxyribonucleic acid (DNA) and where appropriate, ribonucleic acid (RNA). Nucleic acids include but are not limited to single-stranded and double-stranded polynucleotides. Illustrative.

As used herein, the term "vector" refers to a nucleic acid molecule capable of transporting another nucleic acid to which it has been linked. The term "expression vector" refers to a vector comprising a promoter operably linker to a nucleic acid in a manner allowing expression of the operably linked nucleic acid. Vectors or expression vectors as used herein thus include plasmids or phages capable of synthesizing the subject protein encoded by the respective recombinant gene carried by the vector. Vectors or expression vectors also include viral-based vectors capable of introducing a nucleic acid into a cell, e.g., a mammalian cell. Certain vectors are capable of autonomous replication and/or expression of nucleic acids to which they are linked.

As used herein, the term "allele" refers to one specific form of a gene within a cell or within a population, the specific form which may differ from other forms of the same gene in the sequence of at least one, and frequently more than one, variant sites within the sequence of the gene. The sequences at these variant sites that differ between different alleles are termed "variances", "polymorphisms", or "mutations". When a subject has two identical alleles of a gene, the subject is said to be homozygous for that gene or allele. When a subject has two different alleles of a gene, the subject is said to be heterozygous for that gene. Alleles of a specific gene can differ from each other in a single nucleotide or several nucleotides, and can include substitutions, deletions, and insertions of nucleotides. An allele of a gene can also be a form of a gene containing a mutation.

The term "wild-type" refers to a gene or gene product that has the characteristics of that gene or gene product when isolated from a naturally-occurring source. A wild-type gene or gene product (e.g., a polypeptide) is that which is most frequently observed in a population and is thus arbitrarily designed the "normal" or "wild-type" form of the gene.

As used herein, the term "transfection" refers to the introduction of nucleic acid, e.g., an expression vector, into a recipient cell by nucleic acid mediated gene transfer. "Transformation" refers to a process in which a cell's genotype is changed as the result of the cellular uptake of exogenous DNA or R A, and the transformed cell expresses a desired heterologous protein.

As used herein, the term "knock-in (Kin)" refers to the targeted insertion of a transgene in a host cell genome that results in expression of the transgene. "Knock-in" transgenics can comprise a heterozygous knock-in of a transgene. In certain embodiments, a "knock-in" results in the replacement of an endogenous gene (or portion thereof) with an exogenous gene (or portion thereof), e.g., resulting in the targeted mutation of one or both alleles. "Knock-in" also encompasses expression of a transgene by exposing the animal to a substance that promotes such expression, by introducing an enzyme that promotes recombination at the site of targeted insertion (e.g., Cre in Cre-lox system), or by some other method. "Homozygous" state means a genetic condition existing when the same alleles reside at corresponding loci on homologous chromosomes. In contrast, "heterozygous" state means a genetic condition existing when different alleles reside at corresponding loci on homologous chromosomes.

As used herein, the term "CRISPR," "CRISPR system" or "CRISPR nuclease system" and their grammatical equivalents can include a non-coding RNA molecule (e.g., guide RNA) that binds to DNA and Cas proteins (e.g., Cas9) with nuclease functionality (e.g., two nuclease domains).

As used herein, the term "knockout" (abbreviation: KO) is a genetic technique in which one of an organism's genes is made inoperative ("knocked out" of the organism).

As used herein the term "transgene" refers to a nucleic acid sequence which is partly or entirely heterologous, i.e., foreign, to the transgenic animal or cell into which it is introduced, or is homologous to an endogenous gene of the transgenic animal or cell into which it is introduced, but which is designed to be inserted, or is inserted, into the animal's genome in such a way that the genome of the cell to which it is inserted is altered. A transgene can be operably linked to one or more transcriptional regulatory sequences and any other nucleic acid, such as introns, that may be necessary for optimal expression of a selected nucleic acid. Therefore, the term "transgenic" is used herein as an adjective to describe the property of an animal or a construct, of harboring a transgene. For example, "a transgenic animal" is a non-human animal, preferably a non-human mammal, more preferably, a rodent, in which one or more of the cells of the animal contain heterologous nucleic acid introduced by way of human intervention, such as by transgenic techniques well known in the art, including gene knock-in techniques. The nucleic acid is introduced into the cell, directly or indirectly by introduction into a precursor of the cell, via deliberate genetic manipulation, such as by micro-injection or by infection with a recombinant virus. Transgenic animals include, but are not limited to, knock-in animals.

As used herein, the term "expression" is intended to refer to transcription of a gene when a condition is met, resulting in the generation of mRNA and usually encoded protein. Expression can be achieved or performed naturally by the cell (i.e., without artificially intervention) or may be achieved or performed artificially (i.e., with the involvement of artificially intervention, such as by the use of promoters regulated by the use of a chemical agent). The expression may also be initiated by a recombination event triggered by a site-specific recombinase, such as by Cre-mediated recombination. Expression may be measured by measuring mRNA transcribed from the gene or by measuring protein encoded by the gene As used herein, the term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "polypeptide," "peptide" and "protein" are used interchangeably herein to refer to a polymer of amino acid residues.

As used herein, the term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammalis except human.

As used herein, the term "subject" refers to an animal including the human species that may benefit from the method of the present invention. The term "subject" intended to refer to both the male and female gender unless one gender is specifically indicated. Accordingly, the term "subject" comprises any mammal which may benefit from the treatment method of the present disclosure.

As used herein the term "modulate" relates to a capacity to alter an effect or result.

As used herein, the term "transplantation" and variations thereof refers to the insertion of a transplant (also called graft) into a recipient, whether the transplantation is syngeneic (where the donor and recipient are genetically identical), allogeneic (where the donor and recipient are of different genetic origins but of the same species), or xenogeneic (where the donor and recipient are from different species).

As used herein, the term "donor" refers to an animal, preferably a mammal that is the nature source of the bone marrow cells. The donor can be a healthy mammal, that is, a mammal that is not suffering from any obvious disease. Alternatively, the donor can be a mammal suffering from a disease (e.g., cancer). A recipient is an animal, preferably a mammal, receiving the bone marrow cells from a donor. The recipient can be a healthy mammal, that is, a mammal that is not suffering from any obvious disease. Alternatively, the recipient can be a mammal suffering from a disease (e.g., cancer). According to embodiments of the present disclosure, the donor and the recipient can be the same mammal.

As used herein, the term "an effective amount" as used herein refers to an amount effective, at dosages, and for periods of time necessary, to achieve the desired result with respect to the treatment of a disease. For example, in the treatment of a cancer, an agent (i.e., a compound, a polypeptide, a polynucleic acid encoding a therapeutic polypeptide, or a cell engineered to express a therapeutic polypeptide) which decrease, prevents, delays or suppresses or arrests any symptoms of the cancer would be effective. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two or more doses in a suitable form to be administered at one, two or more times throughout a designated time period.

As used herein, the term "treatment" as used herein is intended to mean obtaining a desired pharmacological and/ or physiologic effect, e.g., delaying or inhibiting cancer occurrence, growth, or metastasis, or ameliorating injury to an organ. The effect may be prophylactic in terms of completely or partially preventing or inhibiting occurrence of a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition (e.g., a cancer or heart failure) from occurring in an individual who may be pre-disposed to the disease but has not yet been diagnosed as having it; (2) inhibiting a disease (e.g., by arresting its development); or (3) relieving a disease (e.g., reducing symptoms associated with the disease).

As used herein, the term "administered", "administering" or "administration" are used interchangeably herein to refer a mode of delivery, including, without limitation, intravenously, intramuscularly, intraperitoneally, intraarterially, intracranially, or subcutaneously administering an agent (e.g., a compound or a composition) of the present invention.

As used herein, the term "an effective amount" as used herein refers to an amount effective, at dosages, and for periods of time necessary, to achieve the desired result with respect to the treatment of a disease or condition, such as aging. For example, in the treatment of a cancer, an agent (i.e., a compound, a polypeptide, or a polynucleic acid encoding a therapeutic polypeptide) which decreases, inhibits, prevents, delays or suppresses or arrests any symptoms of the cancer would be effective. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two or more doses in a suitable form to be administered at one, two or more times throughout a designated time period.

As used herein, the term "cell surface marker" means that the subject cell has on its cellular plasma membrane a protein, an enzyme or a carbohydrate capable of binding to an antibody and/or digesting an enzyme substrate. The cell surface markers are recognized in the art to serve as identifying characteristics of particular types of cells.

As used herein, the term "hematopoietic stem cell" refers to a stem cell that is derived from the bone marrow or the blood of a subject. These stem cells are pluripotent and thus have the ability to be transformed into any other type of blood cell or immune cell. Their role within the blood is to keep the body constantly replenished with blood cells as the blood cells must be replaced every day. There are two different types of hematopoietic stem cells, long term and short term. The difference between the two types of cells are that long term can regenerate indefinitely while short term stem cells cannot renew themselves over a long period of time. These long term stem cells have the ability to self-renew while the short term stem cells only are viable for around six months.

As used herein, the term "enhancing longevity" "increasing longevity" and "life-extension" are used interchangeably herein and refer to a delay of the normal aging process and/or prolonging the lifespan of an animal, e.g., an animal suffering from a life-threatening disorder (e.g., a cancer or tumor). Preferably, the longevity is due to an extension of the mature life phase, as opposed to an extension of the immature life phase, and is resulted from being treated by the present method.

As used herein, the term "enhancing health span" refers to a delay in the onset or severity of physical deterioration, diseases, or disorders associated with aging. Enhanced health span also refers to a reduction or reduced amount of physical deterioration, diseases, or disorders normally associated with aging, e.g., at a particular age.

As used herein, the term "allele" refers to one specific form of a gene within a cell or within a population, the specific form which may differ from other forms of the same gene in the sequence of at least one, and frequently more than one, variant sites within the sequence of the gene. The sequences at these variant sites that differ between different alleles are termed "variances", "polymorphisms", or "mutations". When a subject has two identical alleles of a gene, the subject is said to be homozygous for that gene or allele. When a subject has two different alleles of a gene, the subject is said to be heterozygous for that gene.

As used, the term "autologous" refers to a biological material derived from the same individual into whom the material will later be re-introduced.

As used, the term "heterologous" refers to a biological material derived from the different individual into whom the material will later be re-introduced.

As used herein, the term "allogeneic" refers to a biological material derived from a genetically different individual of the same species as the individual into whom the material will be introduced.

Methods of Increasing Longevity and/or Inhibiting or Reducing Tumor Occurrence or Tumor Metastasis In one aspect, the invention provides a method of increasing longevity and/or inhibiting or reducing tumor occurrence or tumor metastasis of a subject, comprising: (a) genetically engineering embryonic stem cells (ESCs), induced pluripotent cells (iPSCs) and/or cord blood stem cells (CBSCs) to possess one or more modified Erythroid Kruppel-like factor (Eklf) genes encoding a modified EKLF polypeptide comprising one or more amino acid modifications as compared to a wild-type EKLF polypeptide; (b) differentiating the genetically engineered ESCs, iPSCs. and/or CSBCs to obtain hematopoietic stem cells (HSCs) and/or hematopoietic stem and progenitor cells (HSPCs); and (c) transplanting the HSCs and/or HSPCs to a subject; whereby the transplanted HSCs and/or HSPCs confer healthy longevity and/or tumor resistance or metastasis resistance to the subject. The invention also provides an in vitro method of obtaining HSCs and/or/HSPCs carrying and expressing one or more modified Eklf genes, comprising genetically engineering ESCs, iPSCs and/or CBSCs to possess one or more modified Eklf genes encoding a modified EKLF polypeptide comprising one or more amino acid modifications as compared to a wild-type EKLF polypeptide; and (b) differentiating the genetically engineered ESCs, iPSCs, and/or CSBCs to obtain HSCs and/or HSPCs carrying and expressing the one or more modified Eklf genes, wherein the HSCs and/or HSPCs confer healthy longevity and/or tumor resistance or metastasis resistance. Alternatively, the present invention provides a use of ESCs, iPSCs, CSBCs HSCs and/or HSPCs in the manufacture of a medicament for increasing longevity and/or inhibiting or reducing tumor occurrence or tumor metastasis of a subject, wherein the ESCs, iPSCs, CSBCs HSCs and/or HSPCs carry and express one or more modified Eklf genes encoding a modified EKLF polypeptide comprising one or more amino acid modifications as compared to a wild-type EKLF polypeptide.

In another aspect, the present invention provides a method of increasing longevity and/or inhibiting or reducing tumor occurrence or tumor metastasis in a receipt subject, comprising: (a) collecting bone marrow from a donor subject comprising one or more modified Eklf genes encoding a modified EKLF polypeptide comprising one or more amino acid modifications as compared to a wild-type EKLF polypeptide; (b) isolating bone marrow mononuclear cells (BMMNCs) comprising HSCs and/or HSPCs HSC and/or HSPC carrying the one or more modified Eklf genes; and (c) transplanting the BMMNCs to a receipt subject, whereby the receipt subject is conferred with tumor resistance and/or healthy longevity. Alternatively, the present invention provides an in vitro method of obtaining HSCs and/or HSPCs expressing one or more Eklf genes that have tumor resistance and healthy longevity character, comprising (a) genetically engineering the BMMNCs to possess one or more modified Eklf genes encoding a modified EKLF polypeptide comprising one or more amino acid modifications as compared to a wild-type EKLF polypeptide; and isolating HSC and/or HSPC carrying the one or more modified Eklf genes. The present invention also provides a use of genetically engineering the BMMNCs in the manufacture of a medicament for increasing longevity and/or inhibiting or reducing tumor occurrence or tumor metastasis in a subject, wherein the BMMNCs having one or more modified Eklf genes encoding a modified EKLF polypeptide comprising one or more amino acid modifications as compared to a wild-type EKLF polypeptide.

Accordingly, the invention provides a cell engineered with a gene encoding a EKLF polypeptide, which comprises at least one amino acid modification as compared to a wild type EKLF polypeptide, wherein the cell is an ESC, an iPSC, a CBSC, a HSC, a HSPC or a BMMNC.

Particular embodiments are directed to ESCs, iPSCs, CBSCs or BMMCs having one or more modified Eklf genes encoding a modified EKLF polypeptide comprising one or more amino acid modifications as compared to a wild-type EKLF polypeptide. In some embodiments, the cell comprises DNA encoding modified EKLF polypeptide at one or both EKLF loci. In some embodiments, the cell comprises DNA encoding modified EKLF polypeptide at one EKLF locus. In certain embodiments, the cell comprises DNA encoding modified EKLF polypeptide at both EKLF loci. In particular embodiments, the cell expresses the modified EKLF polypeptide.

In some embodiments, the one or more amino acid modification comprises a modification of an amino acid corresponding to position 74 of the full length wild-type mouse EKLF polypeptide. In certain embodiments related to animals other than mice, the one or more amino acid modification comprises a modification of a sumoylatable amino acid residue corresponding to this residue in the mouse EKLF polypeptide, but it may be located at a different position. For example, in the human EKLF polypeptide, the sumoylation site corresponding to position 74 in the mouse EKLF polypeptide is located at amino acid residue 54. In particular embodiments, it is a Lys residue. In certain embodiments, the modification of the amino acid corresponding to position 74 is a substitution of Lys with Arg (K74R) or with another amino acid that confers tumor resistance and healthy longevity. In other embodiments, the "another amino acid" is His. In the vertebrates other than mouse and human, a modified vertebrate EKLF polypeptide comprises a substitution of the lysine (K) residue corresponding to the sumoylatable site orthologous to the mouse EKLF K74 and human EKLF K54 with an arginine (R) or another amino acid that confers tumor resistance and healthy longevity.

In certain embodiments, the one or more amino acid modifications comprises a modification of an amino acid corresponding to position 54 of the full length wild-type human EKLF polypeptide. In one embodiment, the modification of the amino acid at position 54 is a substitution of Lys, with Arg (K54R) or another amino acid that confers tumor resistance and healthy longevity. In other embodiments, the "another amino acid" is His. In certain embodiments, the one or more amino acid modifications comprises a modification of an amino acid that is phosphorylated, e.g., in the human EKLF polypeptide, such as, but not limited to, a phosphorylated amino acid corresponding to position 68 of the full length wild-type mouse EKLF polypeptide.

A polynucleotide encoding the desired EKLF mutant allele product (i.e., the EKLF having at least one amino acid modification) can be modified from the native Eklf sequence or manufactured de novo and cloned into suitable expression vectors by any know methods in the related art. Typically, the polynucleotide carrying the desired Eklf mutant allele is operably linked to a suitable control sequence capable of affecting the expression of the desired EKLF mutant polypeptide in the cells. In particular embodiments, a polynucleotide encoding the EKLF polypeptide is the polynucleotide encoding mouse EKLF protein, and in certain embodiments, the modified codon encodes a modification at amino acid position 74. In particular embodiments, a polynucleotide encoding the EKLF protein is the polynucleotide encoding a human EKLF protein, and in certain embodiments, the modified codon encodes a modification at amino acid position 54. Certain embodiments contemplate that the EKLF polypeptide is sumolyated at lysine at position 74 in mice, at lysine at position 54 in humans, or at a corresponding sumoylation site. Particular embodiments contemplate that the human EKLF polypeptide is sumoylated at lysine at position 54. In certain embodiments, a sumoylation site that corresponds to lysine at position 74 of the mouse EKLF polypeptide is lysine at position 54 of the human EKLF polypeptide. Some embodiments contemplate that modification to lysine 74 with arginine with another amino acid that confers tumor resistance and healthy longevity in mouse EKLF polypeptide, to lysine 54 with arginine or with another amino acid that confers tumor resistance and healthy longevity in human EKLF polypeptide, or to a corresponding sumoylation site in other EKLF polypeptides, prevents sumoylation of the EKLF polypeptide. The modification of the sumoylation site of the EKLF polypeptide in a mammal results in increased longevity, increased life span and increased health span of the mammal, as well as reduced tumorigenesis and reduced tumor metastasis in the mammal. In addition, the role of the EKLF K74R (or EKLF K54R) modification on cancerous cells was tested in melanoma bearing mice. Surprisingly, the expression of EKLF K74R (or EKLF K54R) allele prevents the cancerous melanoma cells from metastasizing and increases longevity.

In a particular embodiment, the polynucleotide encoding the desired EKLF mutant polypeptide is inserted into a vector, e.g., a DNA plasmid, virus, or other suitable replicon. Preferably, the nucleic acid sequence encoding the desired EKLF mutant polypeptide is integrated into the genome of a virus, which is subsequently introduced into bone marrow cells, e.g., the highly purified population of HSCs. Viral vectors suitable for use in the present disclosure include but are not limited to, retrovirus, adenovirus, parvovirus (e.g., adeno-associated virus), corcoavirus, negative strand RNA viruses such as orthomyxovirus (e.g., influenza virus), paramyxovirus (e.g., measles and Sendai), rhabdovirus (e.g., rabies and vesicular stomatitis virus), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus. Examples of retroviruses include but are not limited to, avian leucosis-sarcoma, mammalian C-type, B-type viruses, D-type viruses, HTLV-BLV group, lentivirus, spumavirus. Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses.

Alternatively, the cell is transduced to express the modified EKLF polypeptide via use of clustered regularly interspaced short palindromic repeats (CRISPR) and CRISPR associated proteins (Cas) system, in which at least two vectors are used to respectively transport a Cas enzyme and RNAs that hybridize with the target sequences in genomic loci of the nucleic acid encoding the modified Eklf gene product, into the cell. The Cas enzyme is subsequently recruited by the RNAs that hybridize with the target sequences in genomic loci to cleave the expressed modified Eklf gene product. In some embodiments, the Cas enzyme is a type II CRISPR system enzyme. In some embodiments, the type II CRISPR system enzyme is a Cas9 enzyme. In some embodiments, the Cas9 enzyme is *S. pneumoniae, S. pyogenes*, or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target EKLF sequence.

Packaging cell lines can also be used for generating recombinant viral vectors comprising a recombinant genome which includes a polynucleotide encoding a desired gene product (e.g., ELKF K54R or EKLF K74R polypeptide). The use of packaging cell lines can increase both efficiency and the spectrum of infectivity of the produced recombinant virons. Packaging cell lines useful for generating recombinant viral vectors comprising a recombinant genome which includes a nucleic acid encoding a desired gene product (e.g., the present EKLF having at least one amino acid modification) are produced by transfecting host cells, such as a mammalian host cells, with a viral vector having a nucleic acid encoding the desired gene product integrated into the genome of the virus. Suitable host cells for generating cell lines include cells of a human (e.g., Hela cells), a cow, a pig, a mouse (e.g., embryonic stem cells), a rabbit and a monkey (e.g., COS 1 cells). A suitable host cell for generating a cell line may be an embryonic cell, bone marrow stem cell or other progenitor cell.

Examples of suitable methods for transducing or transforming cells include, but are not limited to, infection, calcium phosphate precipitation, electroporation, microinjection, lipofection, and direct uptake. Such methods are well known in the art. Virus stocks consisting of recombinant viral vectors comprising a recombinant genome which includes a nucleic acid encoding the desired EKLF mutant allele product, are produced by maintaining the transduced cells under conditions suitable for virus production (e.g., in an appropriate growth media and for an appropriate period of time). Such conditions are not critical to the present disclosure and are generally known in the related art.

A recombinant gene encoding a desired nucleic acid product and which is operably linked to control sequence capable of effecting the expression of the desired nucleic acid product in the cells can be integrated into the genome of a virus that enters the particular cells of interest. The cells are genetically altered or transformed to comprise a stably incorporated recombinant gene encoding the desired nucleic acid product. The cells that are genetically altered or transformed in such way can then be examined for expression of the recombinant gene prior to administration to a mammal (e.g., the recipient). For example, the amount of desired gene product (e.g., EKLF K54R or EKLF K74R polypeptide) that are expressed may be measured according to standard method (e.g., by Western blot). In this manner, it can be determined in vitro whether a desired nucleic acid product has been expressed to a suitable level in the transformed cells prior to administration to a mammal.

Genetically altered cells expressing the desired nucleic acid product to a suitable level can be expanded (grown) to certain numbers before being introduced or infused into the recipient subject. Methods for expanding cells are well known in the related art.

Any culture medium suitable for culture of pluripotent stem cells may be used in accordance with the present invention, and several such media are known in the art. For example, a culture medium for culture of pluripotent stem cells may comprise Knockout DMEM, 20% Knockout Serum Replacement, nonessential amino acids, 2.5% FBS, Glutamax, beta-mercaptoethanol, 10 ng/microliter bFGF, and antibiotic. The employed medium may also be a variation of this medium, for example without the 2.5% FBS, or with a higher or lower % of knockout serum replacement, or without antibiotic. The employed medium may also be any other suitable medium that supports the growth of human pluripotent stem cells in undifferentiated conditions, such as mTeSR (available from STEMCELL Technologies), or Nutristem (available from Stemgent), or ES medium, or any other suitable medium known in the art. Other exemplary methods for generating/obtaining pluripotent stem cells from a population of cells grown out of a tissue sample that had been frozen with or without a cryoprotective agent.

The genetically engineered ESCs, iPSCs, and/or CSBCs can be differentiated to obtain HSCs and/or HSPCs. Methods are known in the art for directed differentiation or spontaneous differentiation of pluripotent stem cells, for example by use of various differentiation factors. Differentiation of pluripotent stem cells may be monitored by a variety of methods known in the art. Changes in a parameter between a stem cell and a differentiation factor-treated cell may indicate that the treated cell has differentiated. Microscopy may be used to directly monitor morphology of the cells during differentiation.

In some examples, the cell is human HSC that stain positively for at least one marker selected from the group consisting of, Lin, Sca-1, CD7, CD27, CD34, CD38, CD43, CD45RO, CD45RA, CD59, CD90, CD90.1, CD93, CD105, CD109, CD110, CD111, CD117, CD123, CD131, CD133, CD135(Flt3), CD150, CD166, CD173, CD174, CD184, CD202b, CD243, CD271, CD309, CD338, GATA-2, GATA-3, c-myb, Aiolos, TdT, Ikaros, PU.1, HLA DR, and MHC class I. In other examples, the cell is mouse HSC that stains positively for at least one marker selected from the group consisting of, Lin, Sca-1, CD27, CD34, CD38, CD43, CD59, CD90.1, CD117, CD123, CD127, CD135, CD150, GATA-2, GATA-3, TdT, Ikaros, PU.1, Aiolos, c-myb and MHC class I.

The present invention surprisingly found that EKLF is expressed at a relatively high level in the LT-HSC and depletion of EKLF leads to population changes of different types of hematopoietic/blood cells. Furthermore, EKLF negatively regulates the expression of colony-stimulating factor 2 receptor subunit Csf2rb in LT-HSC and the hematopoietic progenitors (such as MPP, CMP, GMP, and MEP). As a result, LT-HSC gains increased differentiation capability upon depletion of EKLF and consequent increase of Csf2rb. The regulation of hematopoiesis by an EKLF-CSF2RB axis starting from LT-HSC and throughout the mono-myeloid lineage and EKLF maintains the homeostasis of LT-HSC in part through prevention of LT-HSC from over-differentiation into the downstream hematopoietic progenitor cells. In one embodiment, the depletion of EKLF increases expression of Csf2rb in LT-HSC. In another embodiment, the expression of EKLF reduces expression of Csf2rb in the hematopoietic stem cells/progenitors. EKLF acts as a repressor to prevent superfluous Csf2rb expression and consequently the differentiation of LT-HSC.

Given the above, the invention shows that depletion of EKLF expression greatly changes the populations of different types of hematopoietic cells including, unexpectedly, the long-term hematopoietic stem cells (LT-HSC). In interesting correlation, EKLF is expressed at a relatively high level in LT-HSC as well as in the multipotent progenitor (MPP).

Furthermore, EKLF appears to repress the expression of the colony-stimulating factor 2 receptor alpha subunit (CSF2RB), known as the common subunit of the receptors for IL-3, GM-CSF and IL-5, in LT-HSC, MPP, GMP, and CMP. As a result, LT-HSC gains increased differentiation capability upon depletion of EKLF and consequent increase of CSF2RB. These results together demonstrate the regulation of hematopoiesis by an EKLF-CSF2RB axis starting from LT-HSC and throughout the mono-myeloid lineage.

According to certain embodiments of the present invention, the cells are genetically engineered in vitro according to the modified Eklf genes, the modified EKLF polypeptides and the transduction (or transfection) methods described herein. Embryonic stem cells (ESCs) can be isolated from blastocysts of members of the primate species. Human embryonic stem (hES) cells can be prepared from human blastocyst cells using the techniques described by Thomson et al. (Science 282:1145, 1998; Curr. Top. Dev. Biol. 38:133 ff., 1998) and Reubinoff et al, Nature Biotech. 18:399, 2000. iPSCs generally have an hESC-like morphology, growing as flat colonies with large nucleo-cytoplasmic ratios, defined borders and prominent nuclei. In addition, iPSCs generally express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Illustrative iPSCs are cells into which the genes Oct-4, Sox-2, c-Myc, and Klf have been transduced. Other exemplary iPSCs are cells into which OCT4, SOX2, NANOG, and LIN28 have been transduced. One of skill in the art would know that various different cocktails of reprogramming factors can be used to produce iPSCs, such as factors selected from the group consisting of OCT4, SOX2, KLF4, MYC, Nanog, and Lin28. Cord blood stem cells are multipotent and are believed to have the ability to form into different stem cell types, which can be isolated from umbilical cord blood remained in the placenta and in the attached umbilical cord after childbirth.

According to certain embodiments of the present invention, the cells are obtained from animals that are genetically altered to express the desired nucleic acid product, such as from the knock-in (Kin) mice that express EKLF K74R (or EKLF K54R) polypeptides. In such embodiments, transgenic Kin mice carrying the desired EKLF K74R mutant allele are created by use of the Cre-loxP recombination system, or by any other method well known in the art, such as site-directed recombination systems. The transgenic animals are screened and evaluated to select those animals having the phenotype of interest. Initial screening can be performed using, for example, Southern blot analysis or PCR techniques to analyze animal tissues to verify that integration of the transgene has taken place. The level of mRNA expression of the transgene in the tissues of the transgenic animals can also be assessed using techniques which include, but are not limited to, Northern blot analysis of tissue samples obtained from the animal, in situ hybridization analysis, and reverse transcriptase-PCR (RT-PCR). Samples of the suitable tissues can be evaluated immuno-cytochemically using antibodies specific for the transgene. Alternative or additional methods for evaluating the presence of the transgene include, but are not limited to, suitable biochemical assays such as enzyme and/or immunological assays, histological stains for particular marker or enzyme activities, flow cytometric analysis, and the like. Analysis of the blood may also be useful to detect the presence of the transgene product in the blood.

According to other embodiments of the present disclosure, the cells are isolated from a normal healthy donor mammal, then are genetically altered to express the desired nucleic acid product (i.e., human EKLF K54R polypeptides), these genetically altered cells are then expanded and administered to a recipient mammal.

According to further embodiments of the present disclosure, the cells are isolated from a mammal in need of a treatment, the cells are then genetically altered to express the desired nucleic acid product (i.e., EKLF K54R polypeptides), expanded and returned to the same mammal by transplantation.

Transplantation of Cells

Preferably, the mode of transplantation of the cells to the receipt subject (e.g., a human) is intravenously, including infusion and/or bolus injection, or intraperitoneally by injection. Other modes such as parenteral, muscosal, implant, intramuscular, intradermal, transdermal may also be used. Preferably, the bone marrow cells are administered in a medium suitable for the particular mode and route of administration into a mammal such as phosphate buffer saline.

The present invention surprisingly found that after transplantation of the BMMCs, HSCs or HPSCs carrying and expressing genes encoding modified EKLF polypeptides to a receipt subject, the recipient subject is able to enjoy a longer lifespan, suppress the growth and/or metastasis of tumor cells. Accordingly, the results suggest that the delivery, via transplantation, of autologous or heterologous cells engineered to express an EKLF mutant allele gene product, can provide a new avenue for prolonging lifespan and/or treating cancer of a subject.

The tumor disorder suppressed by the present invention may be any of liver cancer, colon cancer, breast cancer, prostate cancer, hepatocellular carcinoma, melanoma, lung cancer, glioblastoma, brain tumor, hematopoietic malignancies, retinoblastoma, renal cell carcinoma, head and neck cancer, cervical cancer, pancreatic cancer, esophageal cancer, or squama cell carcinoma. In one preferred example, the cellular proliferative disorder is melanoma.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLE

Materials and Methods
Generation of Eklf-KO Mice

C57BL16, or B6, mice (Jackson Laboratory) were used throughout the study. The generation of B6 mouse lines with heterozygous and homozygous knockout of Eklf gene was carried out in the Transgenic Core Facility (TCF) of IMB, Academia Sinica, following the standard protocols. BAC construct containing genetically engineered Eklf locus (for more details, see the legend of FIG. 1A) and E2A-Cre mice were used for the generation of the Eklf-KO mice.

Generation of the EKLF (K74R) Knock-in Mice

Using mouse genomic DNA from C57B/6J ES cells as template, a fragment containing portions of EKLF exon 2 was PCR amplified and used for constructing a target vector. Prior to cloning into the template targeting vector, codon 74 encoded by exon 2 was mutated to code for arginine (K74R) using standard mutagenesis techniques. A neomycin cassette was also constructed into the target vector, in which a PGK-gb2-neo template encodes the neomycin/kanamycin resistance gene which combines a prokaryotic promoter (gb2) for expression of kanamycin resistance in *E. coli* with a eukaryotic promoter (PGK) for expression of neomycin resistance in mammalian cells. In addition, the modified WT DNA was flanked by 'loxP' sites to facilitate its removal. The target construct was then electroporated into C57B/6J ES cells and selected for neomycin resistance. Appropriately targeted ES clones were identified by 5' and 3' Southern blotting. Following removal of the neo cassette and confirmation of the architecture of the modified genomic region encoding EKLF K74R, the ES clones were injected into blastocytes to generate chimera mice. To obtain heterozygous mice containing the knock-in allele, the germline transmitting F1 lines were crossed with EIIa-Cre mice expressing the Cre recombinase in the whole body. The eklf heterozygotes carrying one allele containing the point mutation were intercrossed to achieve the homozygous eklf (K74R) knock-in mice.

TaqMan Gene Expression Assay

RNA was prepared using TRIzol reagent (Invitrogen) and reverse transcribed using oligo-dT primer and SuperScript III Reverse Transcriptase (RT) (Invitrogen) according to standard procedures. Quantitative PCR (qPCR) using the validated TaqMan assays was carried out on an Applied Biosystems 7500 Real-Time PCR System (Applied Biosystems) instrument under default cycling conditions (50° C. for 2 min, 95° C. for 10 min, 95° C. for 15 s, and 60° C. for 1 min for 40 cycles). The relative EKLF (Mm04208330_g1 and Mm00516096_m1; Applied Biosystems) expression levels were determined from a standard curve of serial dilutions of the cDNA samples and then normalized to the β-actin (Actb:Mm00607939_s1; Applied Biosystems) or Gapdh (Mm99999915_g1; Applied Biosystems) expression levels.

Bone Marrow Transplantation (BMT)

The bone marrows of the mice were extracted from Femur, Tibia and Humerus bones of the CD45.2/EKLF (K74R) donor mice (8-10 weeks old) by 27G needle/syringe and 19G needle/syringe, collected and pushed through a strainer, and the hematopoietic stem cell (HSC) pool was then isolated in accordance with the method described by Liou et al. (2014). Recipient CD45.1/WT C57BL/6 mice at the age of 8-10 weeks old were irradiated with lethal dose (10 Gy) or half-lethal dose (5 Gy) of X-ray. The isolated bone marrow HSC mixture was injected into the tail vein of the irradiated recipient mice. The success of the BMT in each recipient mice was confirmed by flow cytometry analysis. At 8-9 weeks post BMT, anti-tumorigenesis was then evaluated by lung colony assay as described below.

Lifespan Measurement

This follows the standard procedures. The life spans of the EKLF (K74R) knock-in mice were followed-up in specific-pathogen-free (SPF) animal facility.

Assay of Resistance to Tumorigenesis

The murine metastatic melanoma cells, B16-F10 ($10^6$ cells/0.2 mL), were injected intravenously into the tail vein (i.v. injection) of EKLF (K74R) Kin mice and wild type mice (3 mice per group), respectively, to examine the potentials of tumor formation from these cells and metastasis. B16-F10 cells were chosen for test because they are derived from C57BL/6 mice and immunologically compatible with the C57BL/6 mice (wild type and EKLF (K74R) knock-in mice). Two weeks later, the mice were killed by asphyxiation with $CO_2$ and their lungs were removed for further examination. Metastatic nodules on the surface of the lungs were measured by image analysis software (Image Inc.). The measurements of tumor number of each mouse were performed 14 days after injection. One important tip for successful colonization assay on the lung was to use the appropriate number of cancer cells used for injection. People usually use 2-3 different doses of the cancer cells for injection. The tumor colonies on the lung then were quantitated and compared at 2-6 weeks after the injection.

Flow Cytometric Analysis and Cell Sorting

Murine E14.5 fetal liver cells were filtered through a 40 mm nylon cell strainer (BD Biosciences) to get single-cell suspension. As listed in Supplementary Table 1, different types of hematopoietic cells were identified with use of different combinations of the following antibodies against cell surface markers: anti-Lin, anti-Sca-1, anti-c-Kit (CD117), anti-CD34, anti-Thy1.1, anti-Flk2, anti-CD16/32, CD11b, anti-CD11c, anti-Ter119, anti-CD42d, anti-CD41, anti-Gr-1, anti-F4/80 and anti-33D1 (BD Biosciences and Bioscience). After immunostaining with the antibodies, the cells were either analyzed with LSRII (BD Biosciences) and FlowJo software (Tree Star) or sorted with FACSAriaII SORP (BD Biosciences).

SUPPLEMENTARY TABLE 1

| Cell type | Surface Markers |
|---|---|
| LT-HSC | $Lin^-$ $c\text{-}Kit^+$ $Sca\text{-}1^+$ $Thy1.1^{lo}$ $Flk2^-$ $CD34^-$ |
| MPP | $Lin^-$ $c\text{-}Kit^+$ $Sca\text{-}1^+$ $Thy1.1^-$ $Flk2^+$ |
| CMP | $Lin^-$ $c\text{-}Kit^+$ $Sca\text{-}1^-$ $CD34^+$ $CD16/32^{int}$ |
| GMP | $Lin^-$ $c\text{-}Kit^+$ $Sca\text{-}1^-$ $CD34^+$ $CD16/32^{hi}$ |
| MEP | $Lin^-$ $c\text{-}Kit^+$ $Sca\text{-}1^-$ $CD34^-$ $CD16/32^{lo/int}$ |
| Monocyte | $CD11b^+$ $CD11c^-$ |
| Macrophage | $F4/80^+$ |
| Dendritic cell | $CD11b^-$ $33D1^+$ |
| Erythrocyte | $Ter119^+$ |
| Magakaryocyte | $CD41^+$ $CD42d^+$ |
| Granulocyte | $CD11b^{hi}$ $Gr^{hi}$ |

RNA Analysis

Total RNAs from murine E14.5 fetal livers were extracted with TRIzol reagent (Invitrogen). Micro-scale RNAs of purified cells were isolated with use of RNAqueous-Micro Kit (Ambion). cDNAs were then synthesized using SuperScript II Reverse Transcriptase (RT) (Invitrogen) for RT-qPCR analysis. Quantitative real-time PCR (qPCR) analysis of the cDNAs was carried out with the LightCycler® 480 SYBR Green I Master (Roche Life Science) and the products were detected by Roche LightCycler LC480 Real-Time PCR instrument. The sequences of the primers used for the qPCR analysis were either home-designed, as shown in Supplementary Table 2, or downloaded from the online database PrimerBank: http://pga.mgh.harvard.edu/primerbank.

SUPPLEMENTARY TABLE 2

| | Forward sequence | Reverse sequence |
|---|---|---|
| Eklf | 5'-GGACACCCAGGAGGACTTC-3' (SEQ ID NO: 7) | 5'-GGGTCCTCCGATTTCAGACTCA-3' (SEQ ID NO: 8) |

SUPPLEMENTARY TABLE 2-continued

| | Forward sequence | Reverse sequence |
|---|---|---|
| Actin | 5'-ATGGAGGGGAATACAGCCC-3'<br>(SEQ ID NO: 9) | 5'-TTCTTTGCAGCTCCTTCGT-3'<br>(SEQ ID NO: 10) |
| Csf2rb | 5'-ACAGAGAACCTAGATCGAGCC-3'<br>(SEQ ID NO: 11) | 5'-GTGTACTCTTCGCTCCACTTG-3'<br>(SEQ ID NO: 12) |
| Stat1 | 5'-CTGAATATTTCCCTCCTGGG-3'<br>(SEQ ID NO: 13) | 5'-TCCCGTACAGATGTCCATGAT-3'<br>(SEQ ID NO: 14) |
| Stat2 | 5'-GCTGTCAAGGTTCTGCAACA-3'<br>(SEQ ID NO: 15) | 5'-CGCTTGGAGAATTGGAAGTT-3'<br>(SEQ ID NO: 16) |

Immunofluorescence Staining Analysis

LSK (Lin$^-$, Sca-1$^+$ and c-Kit$^+$)-CD34$^-$-Flk2$^-$ LT-HSCs purified by flow sorting as described above were suspended and fixed by 1% paraformaldehyde on 4-well culture slide (Millipore Millicell EZ SLIDE), permeabilized with 0.1% (vol/vol) Triton X-100, and stained with mouse anti-mouse-CSF2RB (Gene Tex) or home-made rabbit anti-mouse EKLF (AEK, Shyu et al., 2006). Anti-mouse and anti-rabbit secondary antibodies were conjugated with Alexa Fluor 488 and 543, respectively. 49-6-diamidino-2-phenylindole (DAPI) (Invitrogen) was used for staining of the nucleus. Fluorescence excitation and image expression were achieved with use of LSM710 and LSM510. Image data were analyzed by the Image J software.

Methylcellulose Colony Formation Assay

The assay followed that described by Miller and Lai (2005). Fluorescence-activated cell sorter (FACS)-purified LT-HSCs from mouse fetal liver were cultured in stem cell culture medium (Serum-Free Expansion Media, STEM-CELL). LT-HSCs were replated with the addition of rmSCF, rhIL-6, rmIL-3 but without rhEPO (GF M2534, STEM-CELL) and the numbers of colonies formed were counted 14 days after plating.

Statistics

Significant differences were determined using a two-tailed Student's t-test (Microsoft Excel). p values ≤0.05 were considered significant.

Example 1 Disturbance of Homeostasis of the Hematopoietic Cells Upon Depletion of EKLF To examine the regulatory effects of EKLF on the homeostasis of the hematopoietic system other than the differentiation of erythroid vs. megakarycyte lineages, we first generated a mouse model with Eklf gene-knockout (KO) using the gene targeting approach (FIG. 1A). The homozygous Eklf$^{-/-}$ mice were embryonic lenthal at E14.5 day and the mutant embryos were anemic, exhibiting albino-like phenotype in part due to the lack of globin gene expression (FIG. 1B). We then prepared E14.5 fetal livers from the Eklf$^{+/+}$ (WT) and Eklf$^{-/-}$ mice (KO), respectively, and sorted the cells using flow cytometer after staining with different combinations of antibodies. As expected from previous studies (Frontelo et al., 2007), absence of EKLF led to great loss of the erythrocyte and concomitant increase of megakaryocyte in the E14.5 fetal liver of KO mice (FIG. 1C).

Figure 2:
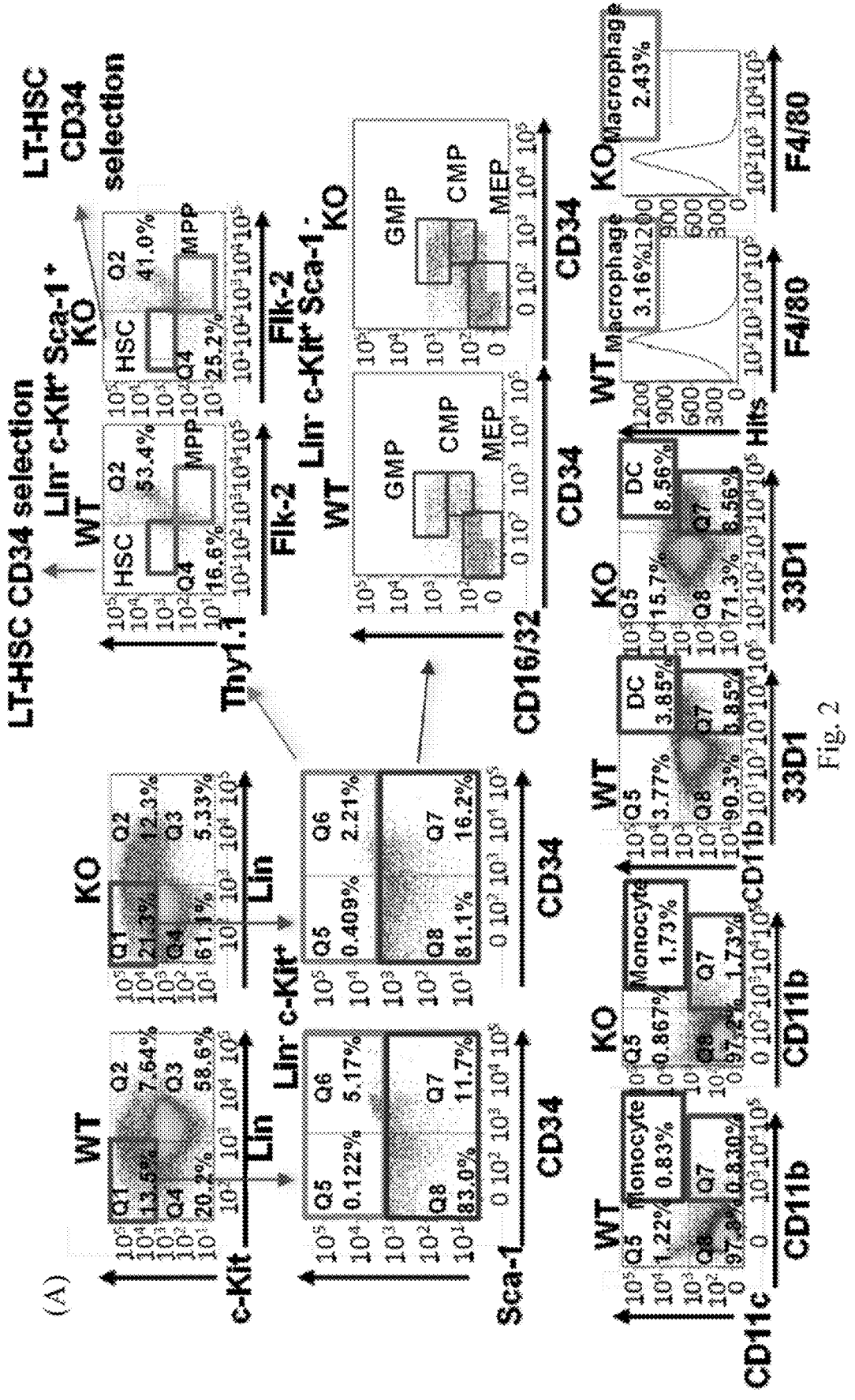
FIGS. 2 (A) and (B) show population changes of the myeloid lineage cells of Eklf$^-$/− E14.5 fetal liver. FACS analysis. Different combinations of antibodies were used to identify LT-HSC (Lin$^-$, CD117$^+$, Sca-1$^+$, Thy1.1$^{lo}$, Flk2$^-$, CD34$^-$), MPP (Lin$^-$, CD117$^+$, Sca-1$^+$, Thy1.1$^-$, Flk2$^+$), CMP (Lin$^-$, CD117$^+$, Sca-1$^-$, CD34$^+$, CD16/32$^{int}$), GMP (Lin$^-$, CD117$^+$, Sca-1$^-$, CD34$^+$, CD16/32$^{hi}$) and MEP (Lin$^-$, CD117$^+$, Sca-1$^-$, CD34$^-$, CD16/32$^{lo/int}$). The differentiated cells were identified as the following: monocyte (CD11b$^+$, CD11c$^-$), dendritic cells (CD11b$^-$, 33D1$^+$), macrophage (F4/80$^+$). The flow data for granulocyte is not shown here. N≥6. (B) Cartoon chart showing the differentiation diagram of hematopoiesis and the population changes of different types of cells in Eklf$^{-/-}$ E14.5 fetal liver in comparison to WT.
Figure 2:
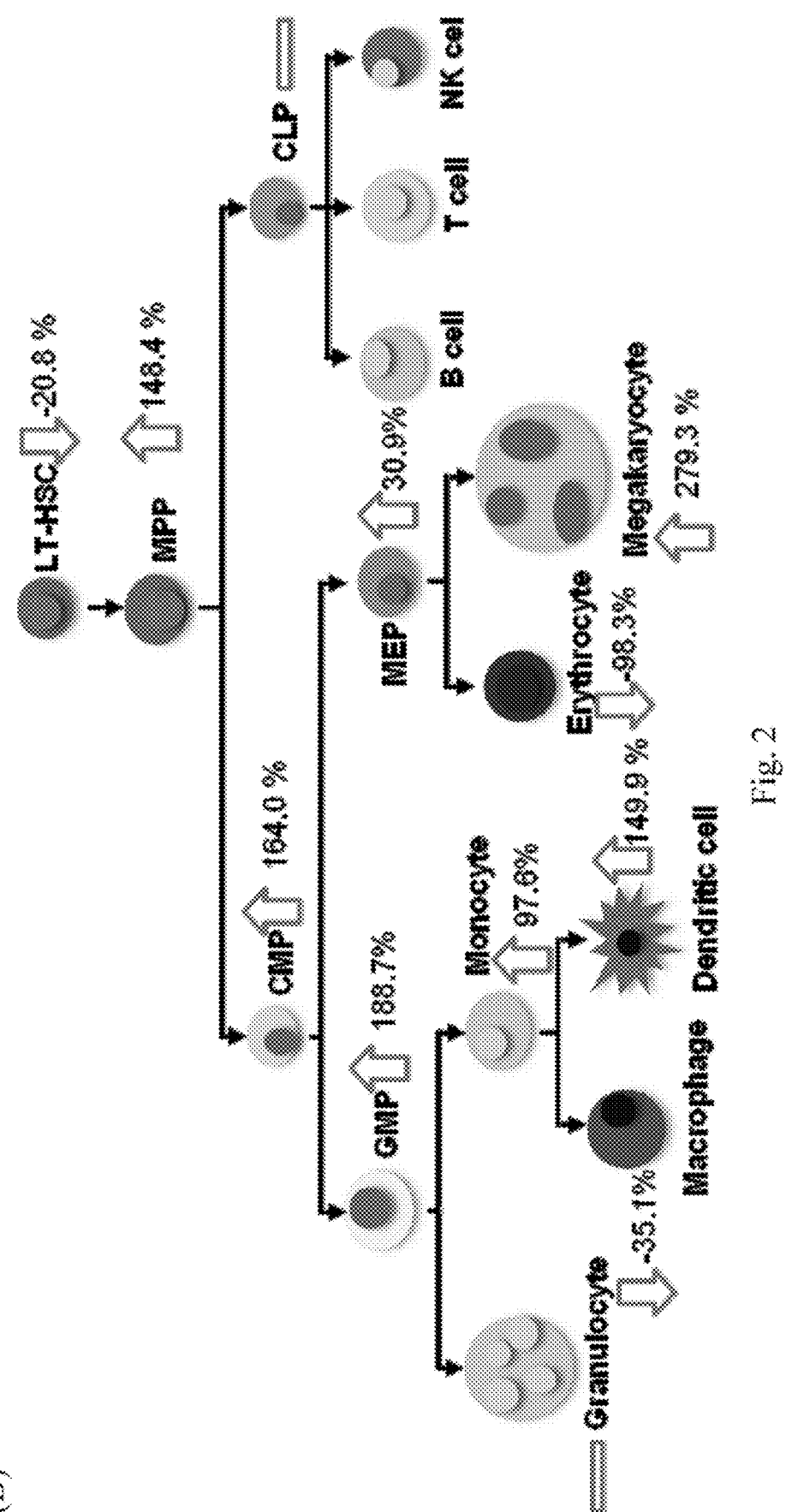

Remarkably, we found that in the KO E14.5 fetal liver, the number of most types of hematopoietic cells, including MPP, CMP, GMP, MEP, monocyte, and dendritic cells, were also increased in comparison to the WT E14.5 fetal liver. On the other hand, CLP and granulocyte remained unchanged, while LT-HSC and macrophage were decreased in their numbers (FIG. 2 and Table 1).

TABLE 1

| | Number/$10^5$ E14.5 Fetal Liver Cells | |
|---|---|---|
| Cell Types | WT | KO |
| LT-HSC | 24 ± 12 | 19 ± 12 |
| MPP | 64 ± 12 | 159 ± 31 |
| CMP | 495 ± 237 | 1,307 ± 496 |
| GMP | 897 ± 372 | 2,590 ± 963 |
| MEP | 10,754 ± 1,489 | 14,082 ± 1,009 |
| Monocyte | 2,289 ± 221 | 4,524 ± 670 |
| Macrophage | 2,577 ± 583 | 1,673 ± 757 |
| Dendritic cell | 5,135 ± 687 | 12,830 ± 601 |

The above data demonstrate that EKLF globally regulates the homeostasis of the hematopoietic system. In particular, the presence of the factor would augment all progenitors in the mono-myeloid lineage. Also, EKLF appears to regulate the homeostasis of LT-HSC as well (see below).

Example 2 Expression Patterns of Eklf and Csf2rb in Hematopoietic Stem Cells and Progenitor To elucidate the molecular basis of the regulatory effects of EKLF on hematopoiesis, we first analyzed and compared the levels of Eklf mRNA in LT-HSC and different hematopoietic progenitors. As shown by RT-qPCR analysis of mRNAs of WT E14.5 fetal liver, the Eklf mRNA level in MEP was comparable to that in the mouse erythroleukemia (MEL) cells, while those in CMP and GMP were fairly low (left histobar diagram, FIG. 3A). This pattern of Eklf expression was similar to that derived from analysis of MEP, CMP, and GMP isolated from the adult mouse bone marrow (Frontelo et al., 2007). Surprisingly, however, the levels of Eklf mRNA in MPP as well as LT-HSC of the E14.5 fetal liver were relatively high, approximately 50% of that of MEP (right 2 bars of the left histobar diagram, FIG. 3A). As expected, Eklf mRNA was absent in the above types of cells of E14.5 fetal liver of KO mice, as exemplified for LT-HSC and MPP (right histobar diagram, FIG. 3A).

The homeostasis of the hematopoietic system depends in part on the balance of the self-renewal of LT-HSC and proliferation of the different hematopoietic precursors with their differentiation capabilities, which are modulated by various cytokines and signal transduction pathways (Ghiaur et al., 2013; Kent et al., 2013; Wang et al., 2013). In view of the population changes of the hematopoietic cells in the E14.5 fetal liver of KO mice (FIG. 1), we carried out

US 12,661,378 B2

Figure 3:
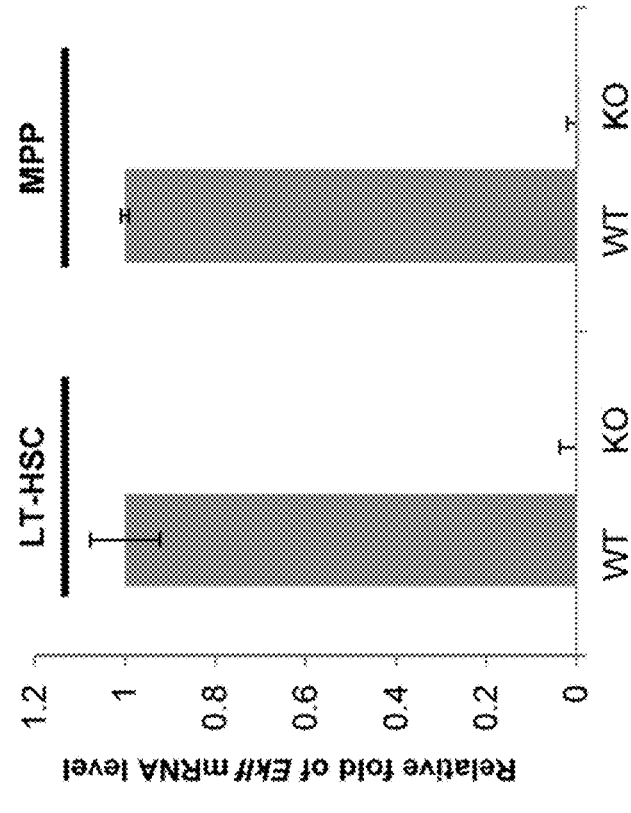
FIGS. 3 (A) and (B) show expression of Eklf and its target gene Csf2rb. (A) RT-qPCR analysis of RNAs isolated from different types of hematopoietic stem cells and progenitors, including LT-HSC, MPP, CMP, GMP and MEP, purified from E14.5 mouse fetal liver by FACS. The relative levels of Eklf mRNA in all of the precursor cells are compared to that of the mouse erythroleukemia (MEL) cells in the left panel with the level in MEP set as 1. The comparative RT-qPCR analysis of Eklf mRNA in LT-HSC and MPP of E14.5 fetal livers from WT and Eklf$^{-/-}$ mice, respectively, is shown in the right panel. (B) RT-qPCR analysis of the mRNA levels of Csf2rb, Stat) and Stat2 in purified CMP, GMP, MEP and MPP. Note the significant increase of Csf2rb mRNA in all four cell types, but increase of Stat2 mRNA only in MEP and increase of Stat) mRNA in MEP as well as MPP. Five biological replicates were analyzed for each type of cells. Each bar represents mean t standard deviation. * p<0.05,  p<0.01, * p<0.001.
Figure 3:
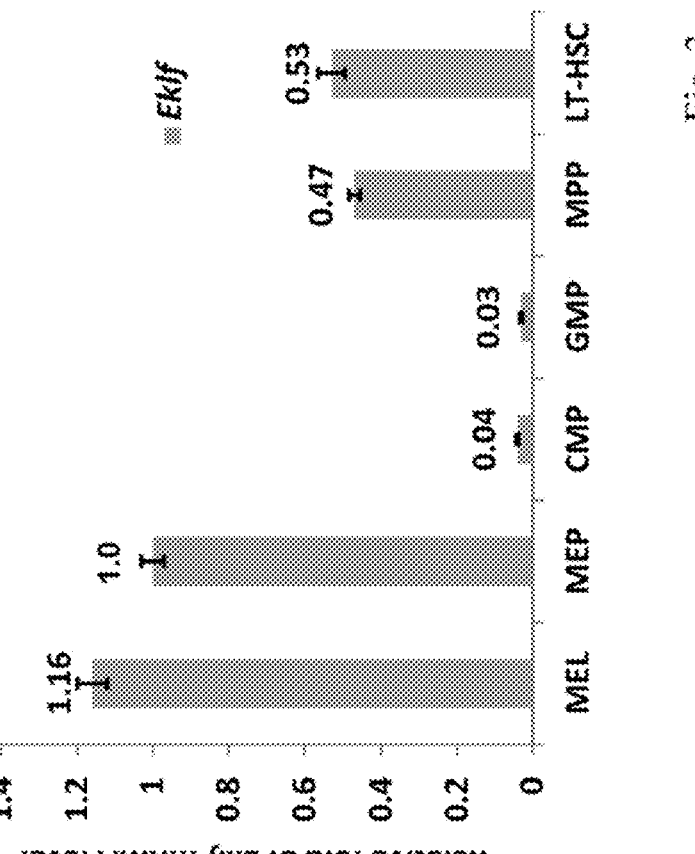
Figure 3:
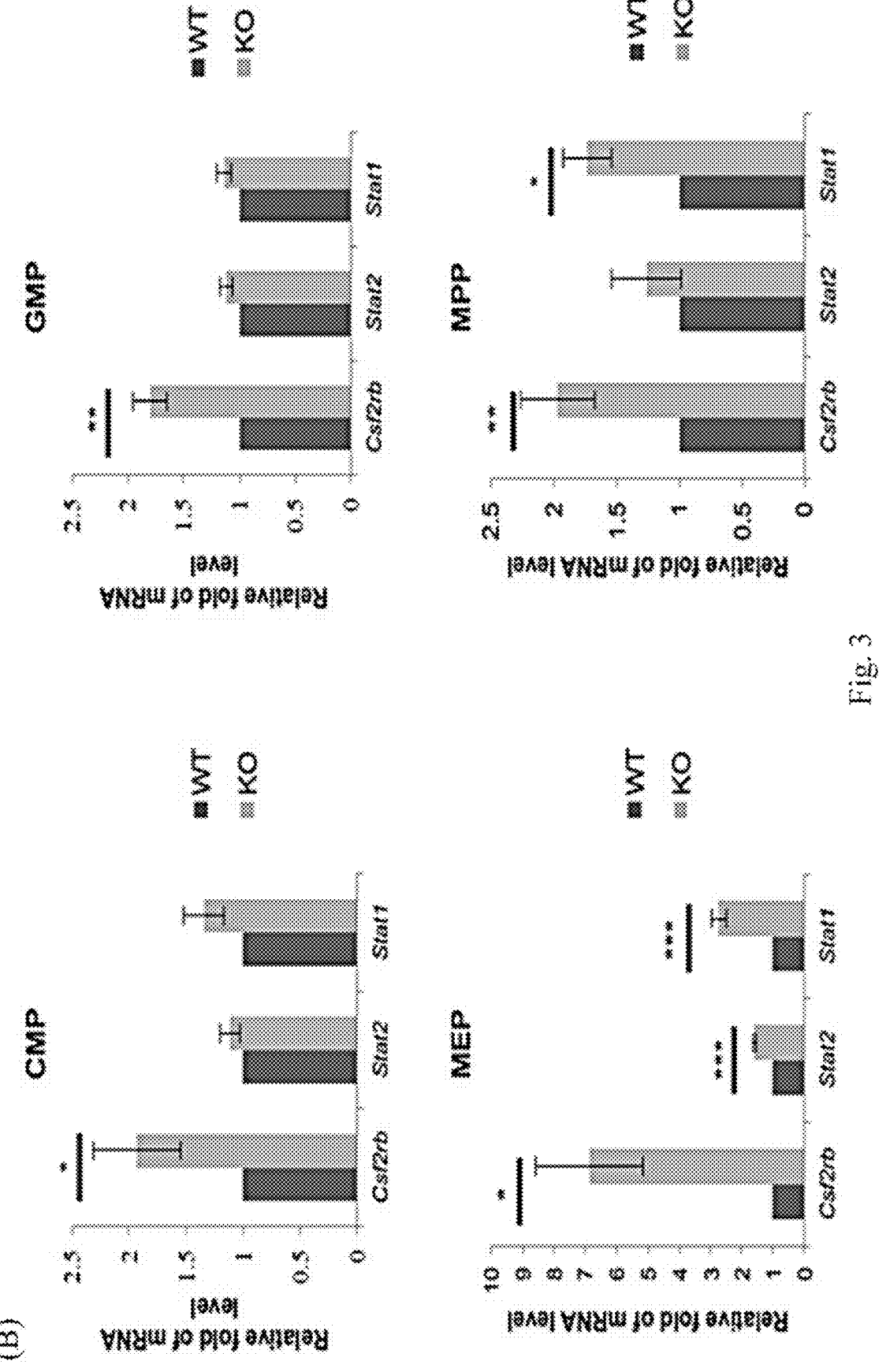

21 quantitative RT-qPCR analysis of the expression of 3 genes, Csf2rb, Stat) and Stat2, known to be involved in the proliferation, self-renewal, and/or maintenance of the hematopoietic stem cells and progenitors (Anam and Davis, 2013). As shown in FIG. 3B, the levels of Stat) mRNA and Stat2 mRNA remained unchanged in CMP and GMP, but they were increased in MEP upon knockout of Eklf. On the other hand, the level of Csf2rb mRNA, which encoded the common subunit CSF2RB of the IL-3/IL-5/GM-CSF receptors, was substantially increased in these three progenitors as well as MPP (FIG. 3B).

Figure 4:
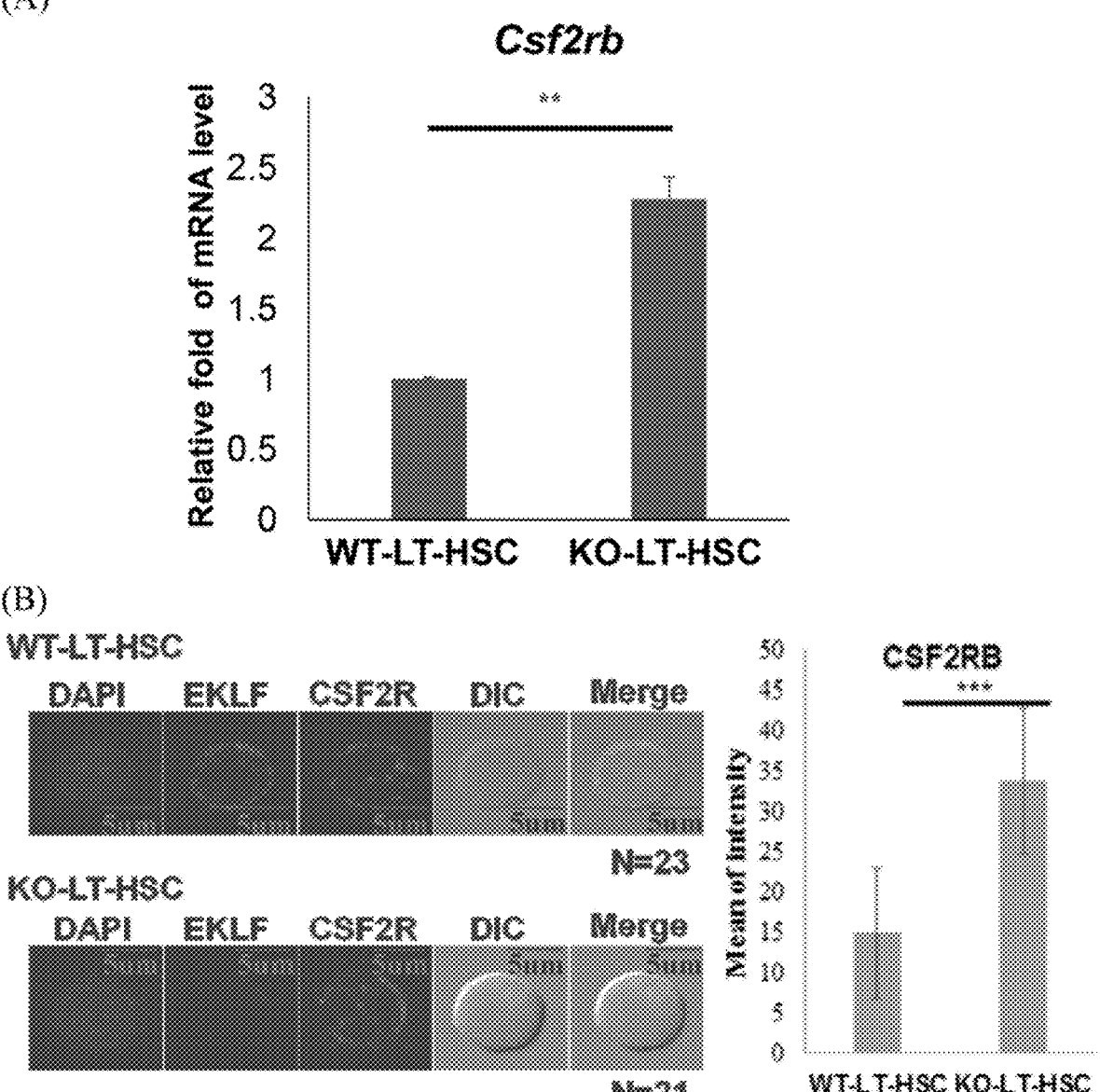
FIGS. 4 (A) to (D) show regulation of LT-HSC differentiation by EKLF. (A) Relative levels of Csf2rb mRNA in LT-HSC purified from WT and KO E14.5 mouse fetal livers were analyzed by RT-qPCR. N≥5. p<0.01. (B) Immunofluorescence staining analysis of the expression of EKLF and CSF2RB in WT-LT-HSC and KO-LT-HSC. DAPI is the nucleus marker. Note the lack of EKLF signal in KO-LT-HSC. Also, signal from staining of the CSF2RB protein in KO-LT-HSC is stronger than that of WT-LT-HSC. Three biological replicates were analyzed. The diameters of LT-HSCs range from 5-10 um. Right panel shows the statistical analysis of the increase of CSF2RB protein in KO-LT-HSC as compared to WT-LT-HSC. p<0.001 (C) Methylcelluose colony assay was performed on WT-LT-HSC and KO-LT-HSC purified (>90%) from E14.5 fetal liver cells by flow cytometry. Note that KO-LT-HSC treated with cytokines/factors for 3-4 weeks displayed around 2.5 folds increase of the colony number when compared to WT-LT-HSC. 1,000 cells per well were used. N≥4. * p<0.001. (D) A simple model showing the regulatory role of EKLF in the homeostasis of LT-HSC, in which it acts as a repressor to prevent superfluous Csf2rb expression and consequently the differentiation of LT-HSC.
Figure 4:
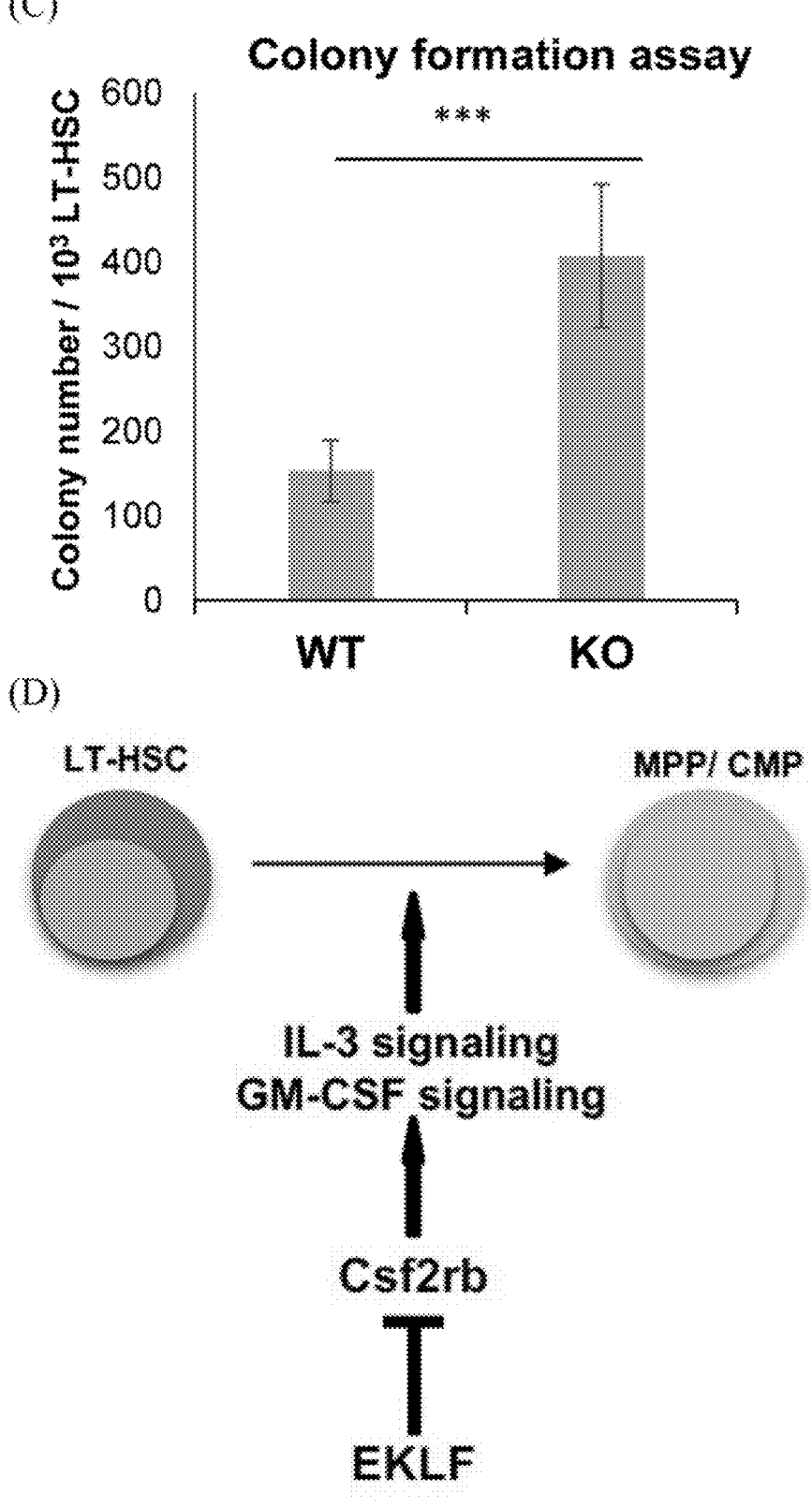

We further analyzed the expression level of Csf2rb mRNA in LT-HSC. As shown in FIG. 4A, Csf2rb mRNA was increased in LT-HSC as well upon depletion of EKLF. Fluorescence co-immunostaining showed that the level of CSF2RB protein was also elevated in LT-HSC of the KO mouse E14.5 fetal liver (FIG. 4B). Interestingly, EKLF was present mainly in the cytosol of LT-HSC (FIG. 4B), a distribution pattern similar to that previously observed in erythroid progenitors (Shyu et al., 2014).

Example 3 Negative Regulation of the Multi-Lineage Differentiation Decision of LT-HSC by EKLF To further understand the basis of the decrease of LT-HSC number in the E14.5 fetal liver of Eklf$^{-/-}$ mice, we carried out the colony formation assay of sorted LT-HSC as described by Miller and Lai (2005). As expected, there was no colony formed when the sorting-purified LT-HSCs from either Eklf$^{+/+}$ or Eklf$^{-/-}$ E14.5 fetal liver were cultured in the cytokine-free methylcellulose medium on plates (data not shown). However, when incubated with the cytokines/factors rmSCF, rhIL-6 and rmIL-3 in the absence of rhEPO, approximately 150 out of 103 WT LT-HSC would form colonies (left bar of the histogram, FIG. 4C). Furthermore, the LT-HSC from Eklf$^{-/-}$ E14.5 fetal liver gained more robust differentiation capacity upon stimulation by the cytokines/factors, as reflected by the 2.5 fold increase of the colony number (right bar of histogram, FIG. 4C). The data of FIG. 4C indicates that under normal conditions, EKLF maintains the homeostasis of LT-HSC in part through prevention of LT-HSC from over-differentiation into the downstream hematopoietic progenitor cells.

Example 4 Transplantation of Bone Marrow of EKLF (K74R) Mice to WT Mice Confers Tumor Resistance in WT Mice The transgenic mouse carrying EKLF K74R mutant allele was generated in according to procedures described in WO 0367272016.

In this example, the CD45.1/wild type mice (the recipient) received transplantation of bone marrow of CD45.2/EKLF (K74R) mice (donors), then tumor resistance of each recipient mice was evaluated by use of the tumor colony assay as described above.

Figure 5:
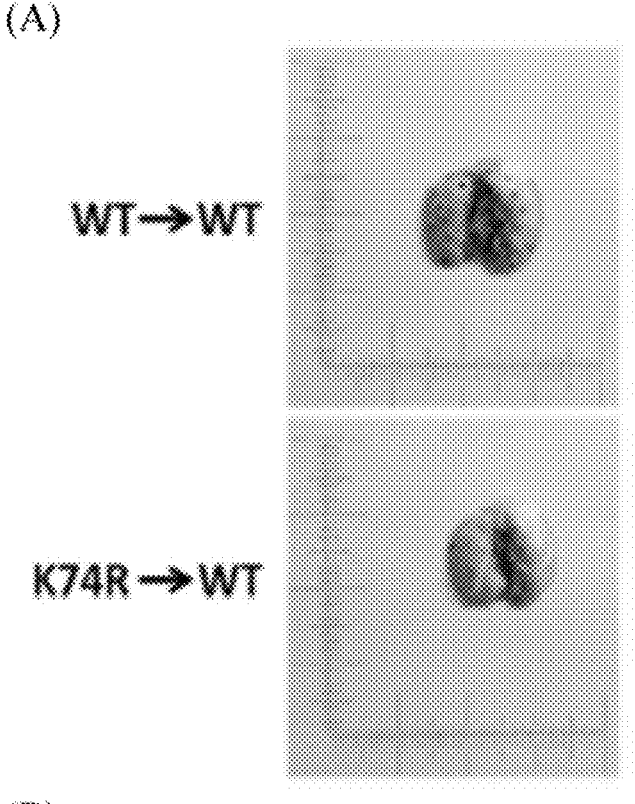
FIGS. 5 (A) and (B) show suppression of cancer in WT mice after bone transplantation from EKLF (K74R) Kin Mice. (A) Representative photos of lungs from WT mice after receiving bone marrow transplantation from WT and Kin mice, respectively. (B) Quantitative presentation of the number of pulmonary foci in the WT mice of panel (A).
Figure 5:
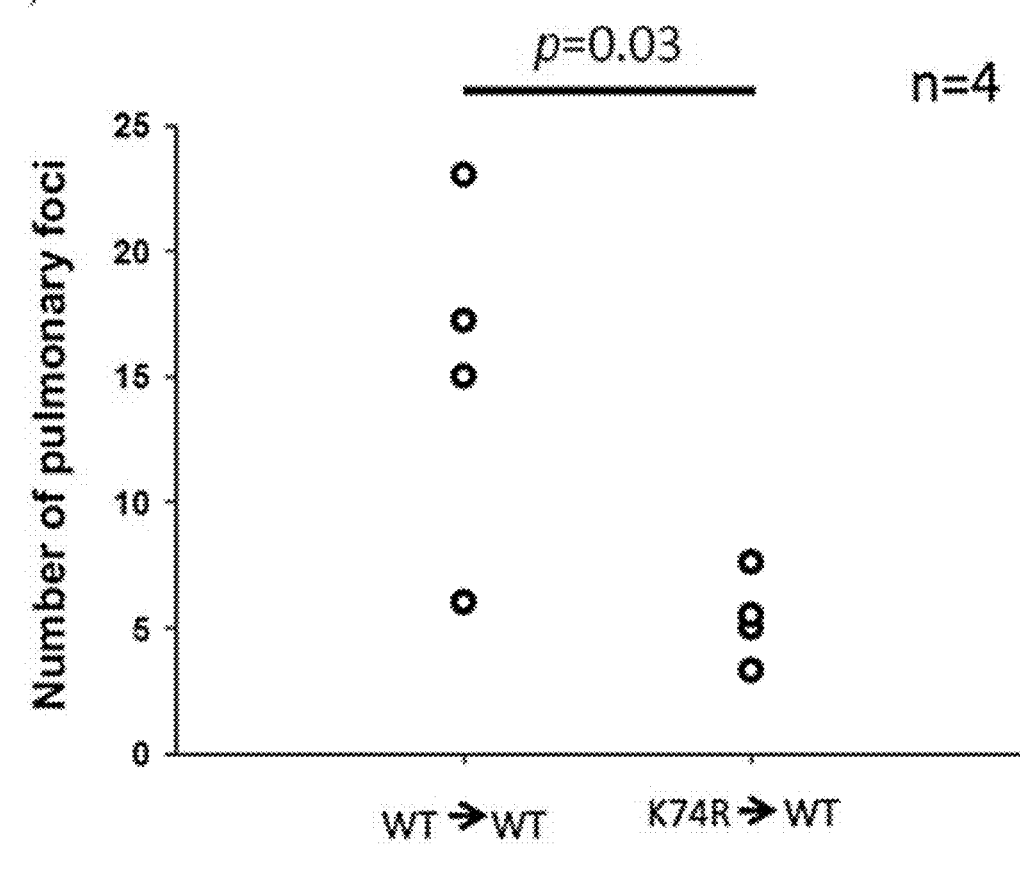

As depicted in FIG. 5A, after transplantation of the bone marrow HSC cells from the EKLF (K74R) mice, the WT mice became much more tumor resistant, as evidenced by the significant decrease in the number of pulmonary foci (about 3-fold lower) induced by the intravenous injection of the melanoma cells (FIG. 5B). The data indicate that the tumor-resistance capability of the EKLF K74R mice is conferred by the genetically engineered hematopoietic/blood system, which could be transferred to other mice by bone marrow transplantation.

We claim:

1. A method of increasing longevity and/or inhibiting or reducing tumor occurrence or tumor metastasis of a subject, comprising:

(a) genetically engineering cord blood stem cells (CBSCs) or bone marrow mononuclear cells (BMMNCs) to possess one or more modified Erythroid Kruppel-like factor (Eklf) genes encoding a modified human EKLF polypeptide comprising an amino acid substitution at the sumoylation site that corresponds to lysine at position 54 of the wild type human EKLF, or a modified mouse EKLF polypeptide comprising an amino acid substitution at the sumoylation site that corresponds to lysine at position 74 of the wild type mouse EKLF; and (b) transplanting the genetically engineered CBSCs or BMMNCs to the subject.

2. The method of claim 1, wherein the CBSCs or BMMNCs are cord blood hematopoietic cells, peripheral hematopoietic cells, hematopoietic stem cells (HSCs), hematopoietic stem and progenitor cells (HSPCs), multipotent progenitors (MPPs), common myeloid progenitors (CMPs), granulocyte/macrophage progenitors (GMPs), myeloid/erythroid progenitors (MEPs), lymphoid cells, or myeloid cells.

3. The method of claim 1, wherein the modified mouse EKLF polypeptide comprises a substitution of the lysine (K) residue corresponding to position 74 of the wild type mouse EKLF with an arginine (R) or with another amino acid that confers tumor resistance and healthy longevity.

4. The method of claim 1, wherein the modified human EKLF polypeptide comprises a substitution of the lysine (K) residue corresponding to position 54 of the wild type human EKLF with an arginine (R) or with another amino acid that confers tumor resistance and healthy longevity.

5. The method of claim 1, wherein the modified mouse EKLF polypeptide comprises an amino acid substitution at position 68 of the full length wild-type mouse EKLF polypeptide.

6. The method of claim 1, wherein the CBSCs or BMMNCs are transduced to express the modified EKLF polypeptide via use of a viral vector encoding the modified EKLF polypeptide.

7. The method of claim 6, wherein the viral vector is derived from a herpes virus, a retrovirus, a vaccinia virus, an attenuated vaccinia virus, a canary pox virus, an adenovirus, or an adeno-associated virus.

8. The method of claim 1, wherein the CBSCs or BMMNCs are transduced to express the modified human EKLF polypeptide or the modified mouse EKLF polypeptide via use of clustered regularly interspaced short palindromic repeats (CRISPR) and CRISPR associated proteins (Cas) system.

9. The method of claim 1, wherein the expression of the modified human EKLF polypeptide or the modified mouse EKLF polypeptide leads to enhanced lifespan, anti-metastasis, and/or anti-tumorigenesis.

10. The method of claim 2, wherein the modified human EKLF polypeptide or the modified mouse EKLF polypeptide is expressed at a relatively high level in long-term (LT)-HSCs and depletion of EKLF leads to population changes of different types of hematopoietic cells or hematopoietic progenitors.

11. The method of claim 2, wherein the modified human EKLF polypeptide or the modified mouse EKLF polypeptide negatively regulates the expression of colony-stimulating factor 2 receptor subunit Csf2rb in LT-HSCs and the hematopoietic cells or the hematopoietic progenitors.

12. The method of claim 1, wherein the tumor is liver cancer, colon cancer, breast cancer, prostate cancer, hepatocellular carcinoma, melanoma, lung cancer, glioblastoma, brain tumor, hematopoietic malignancies, retinoblastoma, renal cell carcinoma, head and neck cancer, cervical cancer, pancreatic cancer, esophageal cancer, or squamous cell carcinoma.

* * * * *

```
SEQUENCE LISTING

<160> NUMBER OF SEQ ID NOS: 16

<210> SEQ ID NO 1
<211> LENGTH: 20
<212> TYPE: DNA
<213> ORGANISM: Artificial sequence
<220> FEATURE:
<223> OTHER INFORMATION: primer(5'-deletion), synthetic sequence

<400> SEQUENCE: 1
gcggcgcgat aacttcgtat                                          20

<210> SEQ ID NO 2
<211> LENGTH: 22
<212> TYPE: DNA
<213> ORGANISM: Artificial sequence
<220> FEATURE:
<223> OTHER INFORMATION: primer(5'-PGK), synthetic sequence

<400> SEQUENCE: 2
ttgaattctg cttcctgttg ga                                       22

<210> SEQ ID NO 3
<211> LENGTH: 22
<212> TYPE: DNA
<213> ORGANISM: Artificial sequence
<220> FEATURE:
<223> OTHER INFORMATION: primer(EKLF-F), synthetic sequence

<400> SEQUENCE: 3
```
aggcagaaga gagagaggag gc                                        22

<210> SEQ ID NO 4
<211> LENGTH: 22
<212> TYPE: DNA
<213> ORGANISM: Artificial sequence
<220> FEATURE:
<223> OTHER INFORMATION: primer(3'-deletion), synthetic sequence

<400> SEQUENCE: 4
cctatttctc caacaggaag ca                                       22

<210> SEQ ID NO 5
<211> LENGTH: 20
<212> TYPE: DNA
<213> ORGANISM: Artificial sequence
<220> FEATURE:
<223> OTHER INFORMATION: primer(PGK-R), synthetic sequence

<400> SEQUENCE: 5
ctggccctca aacaaccctg                                          20

<210> SEQ ID NO 6
<211> LENGTH: 22
<212> TYPE: DNA
<213> ORGANISM: Artificial sequence
<220> FEATURE:
<223> OTHER INFORMATION: primer(3'-PGK), synthetic sequence

<400> SEQUENCE: 6
gttatgcggc cctagtgatt ta                                       22

<210> SEQ ID NO 7
<211> LENGTH: 19
<212> TYPE: DNA
<213> ORGANISM: artificial sequence
<220> FEATURE:
<223> OTHER INFORMATION: Eklf Forward sequence, synthetic sequence

<400> SEQUENCE: 7
ggacacccag gaggacttc                                           19

<210> SEQ ID NO 8
<211> LENGTH: 22
<212> TYPE: DNA
<213> ORGANISM: Artificial sequence
<220> FEATURE:
<223> OTHER INFORMATION: Eklf Reverse sequence, synthetic sequence

<400> SEQUENCE: 8
gggtcctccg atttcagact ca                                       22

<210> SEQ ID NO 9
<211> LENGTH: 19
<212> TYPE: DNA
<213> ORGANISM: Artificial sequence
<220> FEATURE:
<223> OTHER INFORMATION: Actin Forward sequence, synthetic sequence

<400> SEQUENCE: 9
atggagggga atacagccc                                           19

<210> SEQ ID NO 10
<211> LENGTH: 19
<212> TYPE: DNA
<213> ORGANISM: Artificial sequence -continued
<220> FEATURE:
<223> OTHER INFORMATION: Actin Reverse sequence, synthetic sequence

<400> SEQUENCE: 10
ttctttgcag ctccttcgt                                            19

<210> SEQ ID NO 11
<211> LENGTH: 21
<212> TYPE: DNA
<213> ORGANISM: Artificial sequence
<220> FEATURE:
<223> OTHER INFORMATION: Csf2rb Forward sequence, synthetic sequence

<400> SEQUENCE: 11
acagagaacc tagatcgagc c                                         21

<210> SEQ ID NO 12
<211> LENGTH: 21
<212> TYPE: DNA
<213> ORGANISM: Artificial sequence
<220> FEATURE:
<223> OTHER INFORMATION: Csf2rb Reverse sequence, synthetic sequence

<400> SEQUENCE: 12
gtgtactctt cgctccactt g                                         21

<210> SEQ ID NO 13
<211> LENGTH: 20
<212> TYPE: DNA
<213> ORGANISM: Artificial sequence
<220> FEATURE:
<223> OTHER INFORMATION: Stat1 Forward sequence, synthetic sequence

<400> SEQUENCE: 13
ctgaatattt ccctcctggg                                           20

<210> SEQ ID NO 14
<211> LENGTH: 21
<212> TYPE: DNA
<213> ORGANISM: Artificial sequence
<220> FEATURE:
<223> OTHER INFORMATION: Stat1 Reverse sequence, synthetic sequence

<400> SEQUENCE: 14
tcccgtacag atgtccatga t                                         21

<210> SEQ ID NO 15
<211> LENGTH: 20
<212> TYPE: DNA
<213> ORGANISM: Artificial sequence
<220> FEATURE:
<223> OTHER INFORMATION: Stat2 Forward sequence, synthetic sequence

<400> SEQUENCE: 15
gctgtcaagg ttctgcaaca                                           20

<210> SEQ ID NO 16
<211> LENGTH: 20
<212> TYPE: DNA
<213> ORGANISM: Artificial sequence
<220> FEATURE:
<223> OTHER INFORMATION: Stat2 Reverse sequence, synthetic sequence

<400> SEQUENCE: 16
cgcttggaga attggaagtt                                           20